US010610240B2

(12) United States Patent
Downey

(10) Patent No.: US 10,610,240 B2
(45) Date of Patent: Apr. 7, 2020

(54) PRESSURE SENSITIVE ARRANGEMENT AND METHOD FOR USE THEREOF

(71) Applicant: MEMORIAL SLOAN-KETTERING CANCER CENTER, New York, NY (US)

(72) Inventor: Robert J. Downey, Franklin, NJ (US)

(73) Assignee: MEMORIAL SLOAN-KETTERING CANCER CENTER, New York, NY (US)

(*) Notice: Subject to any disclaimer, the term of this patent is extended or adjusted under 35 U.S.C. 154(b) by 331 days.

(21) Appl. No.: 15/102,035

(22) PCT Filed: Dec. 8, 2014

(86) PCT No.: PCT/US2014/069086
§ 371 (c)(1),
(2) Date: Jun. 6, 2016

(87) PCT Pub. No.: WO2015/085302
PCT Pub. Date: Jun. 11, 2015

(65) Prior Publication Data
US 2016/0310149 A1    Oct. 27, 2016

Related U.S. Application Data

(60) Provisional application No. 61/913,079, filed on Dec. 6, 2013.

(51) Int. Cl.
*A61B 17/135* (2006.01)
*A61B 5/0225* (2006.01)
*A61B 17/00* (2006.01)

(52) U.S. Cl.
CPC ...... *A61B 17/1355* (2013.01); *A61B 5/02255* (2013.01); *A61B 2017/00057* (2013.01);
(Continued)

(58) Field of Classification Search
CPC .. A61M 5/425; A61B 17/135; A61B 17/1355; A61B 17/1322; A61B 5/0225; A61B 5/02255
See application file for complete search history.

(56) References Cited

U.S. PATENT DOCUMENTS 5,316,005 A    5/1994  Tomita
2002/0016610 A1    2/2002  Hovanes et al.
(Continued)

FOREIGN PATENT DOCUMENTS

EP    0298620    1/1989
EP    0333449    9/1989
(Continued)

OTHER PUBLICATIONS

Extended European Search Report dated Jun. 20, 2017 for European National Phase Application No. 14868080.4.
(Continued)

*Primary Examiner* — Thomas M McEvoy
(74) *Attorney, Agent, or Firm* — Hunton Andrews Kurth LLP

(57) ABSTRACT

Exemplary systems, methods and computer-accessible mediums can be provided that can, for example, receive information related to a detection of a pulse of a patient(s), and increase a pressure using a hardware arrangement to reach a first pressure level corresponding to the pulse no longer being detected. The pressure can be decreased to reach a second pressure level corresponding to the pulse being again detected, and the pressure can be maintained at the second pressure level to facilitate a venipuncture of the patient(s).

19 Claims, 20 Drawing Sheets

(52) U.S. Cl.
CPC ............... *A61B 2017/00119* (2013.01); *A61B 2562/0204* (2013.01)

(56) References Cited

U.S. PATENT DOCUMENTS

2010/0331709 A1  12/2010  Matsumura et al.
2014/0336697 A1* 11/2014  Masaki ................ A61B 17/135
                                                        606/203

FOREIGN PATENT DOCUMENTS

| EP | 1252861 | | 10/2002 |
|---|---|---|---|
| JP | 2009-95516 | * | 5/2009 |
| JP | 2009-95516 A | | 5/2009 |
| WO | WO 2013/084912 | | 6/2013 |

OTHER PUBLICATIONS

International Search Report for International Application No. PCT/US2014/069086 dated Mar. 4, 2015.
International Written Opinion for International Application No. PCT/US2014/069086 dated Mar. 4, 2015.
Steinke, J.M. et al., "Role of Light Scattering in Whole Blood Oximetry," IEEE Transactions on Biomedical Engineering, Mar. 1986, vol. 33, No. 3, pp. 294-301.
Solid Angle—from Wolfram Math World, http://mathworld.wolfram.com/SolidAngle.html, Mar. 3, 2013.
Bhandari N. "A Simple Relationship between the Transistor Parameters hFE and hfe," Proceedings of the IEEE, 1967, vol. 55, p. 1099.
NPN Transistor, http://i.stack.imgur.com/m9rv6.png, Feb. 24, 2013.
Anderson, A.E. et al., "Transistors in Switching Circuits," Proceedings of the IRE, 1952, vol. 40, pp. 1541-1558.
KSV05A Solenold Valve Data Sheet, http://www.koge.com/UploadFile/pdf/2011325142159-KSV05A.pdf, Accessed Feb. 24, 2013.
KPM14A Air Pump Data Sheet, http://www.koge.com/UploadFile/pdf/2011324115349-KPM14A.pdf, Feb. 24, 2013.
Serway, R.A. et al., "Physics for Scientists and Engineers with Modern Physics," 7th Edition, Thomson Learning, Belmont, 2008, pp. 869.
Serway,R.A. et al., "Physics for Scientists and Engineers with Modern Physics," 7th Edition, Thomson Learning, Belmont, 2008, pp. 850.
Serway, R.A. et al., "Physics for Scientists and Engineers with Modern Physics," 7th Edition, Thomson Learning, Belmont, 2008, pp. 849.
Pilliner,G.W. "Protection and Safety Part 6: Electromagnetic Problems," Electronic Systems News, 1988, pp. 19 and 20.
Holubkov, R. et al. "Large Brachial Artery Diameter is Associated with Angiographic Coronary Artery Disease in Women," American Heart Journal, 2002, vol. 143, pp. 802-807.
Spivack, D.E. et al., "Mapping of Superficial Extremity Veins: Normal Diameters and Trends in . . . ," Ultrasound In Medicine Biology, 2012, vol. 38, pp. 190-194.
Ku, D.N., "Blood Flow in Arteries," Annual Review of Fluid Mechanics, 1997, vol. 29, pp. 399-434.
Ethier, C.R. et al., "Introductory Biomechanics: From Cells to Organisms," 1st Edition, Cambridge University Press Cambridge, 2007, pp. 190.
Weidinger, Franz et al., "Association of Wall Thickness of the Brachial Measured with High-Resolution . . . ," American Journal Cardiology, May 1, 2002, vol. 89, pp. 1025-1029.
Jaberi, A. et al.,"Arteriovenous Fistulas for Hemodialysis: Application of High-Frequency US to Assess Vein Wall . . . ," Radiology, Nov. 2011, vol. 261, pp. 616-624.
Tracy, R.E, et al., "Coronary Artery Circumferential Stress: Departure from Laplace Expectations with Aging," Scientific World Journal, 2009, vol. 9, pp. 946-960.
Arduino Mini. http://arduino.cc/en/uploads/Main/Mini05_front.jpg, May 18, 2013.
Arduino Mini and NG Breadboard, http://arduino.cc/en/uploads/Guide/ArduinoMiniAndNGBreadboardPhoto.jpg, May 18, 2013.
Radioshack 12V/20MA 4MM Red Led with Holder. Accessed May 18, 2013 and Jan. 20, 2017; http://www.radioshack.com/product/index.jsp?productId=276270.
Green LED with Holder, RadioShack. Accessed May 18, 2013 and Jan. 20, 2017; http://www.radioshack.com/product/index.jsp?productId=276271.
RadioShack LED with Holder (Orange), RadioShack. Accessed May 18, 2013 and Jan. 20, 2017; http://www.radioshack.com/product/index.jsp?productId=276272B.
Truskey, George A. et al., "Transport Phenomena in Biological Systems," 2nd Edition, Pearson Prentice Hall, Upper Saddle River, 2009, p. 63.
Truskey, George A. et al., "Transport Phenomena in Biological Systems," 2nd Edition, Pearson Prentice Hall, Upper Saddle River, 2009, p. 93.
Truskey, George A. et al., "Transport Phenomena in Biological Systems," 2nd Edition, Pearson Prentice Hall, Upper Saddle River, 2009, p. 109.
Communication pursuant to Articie 94(3) EPC dated Oct. 26, 2018 based on European Patent Applicatno No. 14868080.4.
Examination Report No. 1 dated Aug. 22, 2018 for Australian Patent Application No. 2014360117.

* cited by examiner

SOLDER MASK BOTTOM

LAYER SLIKSCREEN TOP

LAYER 2 GROUND

LAYER 1 COMP SIDE

LAYER 4 SOLDER SIDE

LAYER 2 POWER

LAYER SOLDER PASTE TOP

LAYER SOLDER MASK TOP

PRESSURE SENSITIVE ARRANGEMENT AND METHOD FOR USE THEREOF

CROSS-REFERENCE TO RELATED APPLICATION(S)

The present application relates to and claims the benefit and priority from International Patent Application No. PCT/US2014/069086, filed on Dec. 8, 2014, which claims the benefit and priority from U.S. Provisional Patent Application No. 61/913,079, filed on Dec. 6, 2013, the entire disclosures of which are incorporated herein by reference in their entireties.

FIELD OF THE DISCLOSURE

The present disclosure relates generally to an exemplary system, method and computer-accessible medium, which can be provided with or can be in cooperation with a pressure sensitive tourniquet arrangement, and which can provide and/or maintain pressure for use in a venipuncture.

BACKGROUND INFORMATION

Venipuncture and peripheral intravenous catheter insertion are routine medical procedures performed to collect blood samples, and to administer medications or body fluids. In 2008, there were about 37.5 million hospital admissions in the U.S., and almost every hospital patient can have at least one blood draw on admission. Additionally, 7 out of 10 patients can receive an IV, and 3 out of 10 patients can get an injection of contrast, which can total a minimum of 263 million vein access procedures in the year 2008 alone. This figure does not include any vein access procedures done during an out-patient procedure. Based upon the industry's recognized vein access failure rate of about 40%, which can result in a multiple stick event for 4 out of every 10 patients (e.g., on every stick attempt), this adds up to a minimum estimate of 174 million vein access failures divided between the IV, the blood draw, and the injection of contrast. (See, e.g., The National Phlebotomy website (http://www.nationalphlebotomy.org/).

An extraction of blood from a peripheral vein, or the insertion of catheter, usually benefits from a distention of superficial veins in the arm. For a successful venous distention, the venous flow should be occluded while the arterial flow should unhinder. Ideally, for example, the optimal venous distension can be caused by applying a pressure between the systolic and diastolic pressures.

The current technique for accessing an extremity vein includes placing a tourniquet proximal (e.g., nearer the heart) on the extremity. The tourniquet is most commonly made of an elastic material (e.g. a rubber glove, or a rectangular piece of elastic material), and as such, it can be difficult or even impossible to measure the pressure applied. Therefore, the applied pressure can be above the arterial systolic pressure, which can result in no blood inflow, or the pressure can be below the arterial diastolic pressure, facilitating venous outflow. In both cases, venous distension may not occur. An optimal pressure for the tourniquet would be below the systolic pressure (e.g., the peak arterial pressure), and above the diastolic pressure (e.g., the venous pressure). Applying this pressure can facilitate an arterial inflow, but would likely not facilitate a venous outflow, thereby leading to the distension of the circulation.

The pliable strap or latex strip tourniquet can be commonly used by positioning it around the arm of the patient. Both ends can be grasped and tied to apply a small amount of tension. It can be the least expensive, and is a disposable tourniquet, and it can prevent cross infection of patients, as it does not readily support bacterial growth because of the material property of latex. In addition, it can be easily cleaned with any disinfectant. However, the pliable strap tourniquet cannot be loosened gradually, which can pinch the skin on elderly patients. It also needs nurses and technicians to use both hands for proper positioning.

A Velcro® closure tourniquet can be made of elastic material with a long band that facilitates a wider range of adjustments. Generally, the Velcro® tourniquet can be more expensive than the pliable strap tourniquet. It can be easily cleaned with any disinfectant. In addition, the Velcro® tourniquet can be easier to apply and release than the pliable strap tourniquet. The Velcro strap, however, cannot be loosened gradually, and it also likely needs using both hands for proper positioning.

The buckle closure tourniquet can be made of cloth fabric with a buckle closure (e.g., seat-belt design). It can be gradually loosened and tightened again, if necessary. Unlike the tourniquets above, it may not be disposable, and cannot be easily cleaned with disinfectants. Generally, the buckle closure tourniquet is not commonly used because of its high cost and restricted usage.

A common blood pressure cuff can be used as a tourniquet. The cuff can be inflated to a pressure between the systolic and diastolic pressures for venous distension. It can be useful among patients with weak veins that can be difficult to see with the naked eyes. Blood pressure cuffs usually include a sphygmomanometer, thus, the applied pressure can be readily known.

In the surgical setting, surgical tourniquets can be applied to the limb occlusion pressure ("LOP"), the minimum pressure used to occlude a patient's limb completely, to localize anesthesia drugs and to provide a bloodless operating field during surgeries. There are many different surgical tourniquet systems. A surgical tourniquet can consist of an instrument for pressure regulation, and an inflatable cuff for pressure application. It can be designed to measure the LOP using the ascending LOP measurement technique. The ascending LOP measurement can determine the LOP by slowly increasing pressure in the cuff until the LOP can be reached.

This surgical tourniquet generally requires the surgical staffs to enter an estimated LOP value. This LOP value can be set as the reference pressure, and can be regulated by a controller during surgeries every 40 millisecond with the allowed deviation of ±15 mmHg. A pulse oximeter can be utilized as a means to adjust the preset reference pressure. The pulse oximeter can be composed of an infrared LED with wavelength of about 915 nm, and a photodiode that can be sensitive to that wavelength. The basic principle of pulse measuring can be based on the absorption of infrared light by oxygenated hemoglobin. Based on oxygenated hemoglobin concentration, current can be produced by the photodiode. This current can be filtered, sampled and analyzed by the controller. However, concentration of oxygenated hemoglobin in the extremity can be time-varying, in synchrony with the cardiac cycle. As a result, time-varying current signifies incomplete occlusion of arterial flow. The preset reference pressure can be adjusted according to the pulse detection in the extremity. A new reference pressure can be obtained when no time-varying current can be detected. This pressure will be the LOP and it will be maintained until the end of surgeries. The A.T.S. 3000 Automatic Tourniquet System is a medical tourniquet system with a processor controlling two air pressure ports at each cuff. One port can be used for pressure measurement, while the other port regulates cuff pressure. It uses a LOP sensor at the patient's index finger or toe to provide a recommended LOP to the surgeon. However, this pressure can be used to completely occlude the patient's limb.

Thus, it may be beneficial to provide an exemplary pressure sensitive device that can reduce the rate of vein access failure for an individual patient's blood pressure, and which can overcome at least some of the deficiencies described herein above.

SUMMARY OF EXEMPLARY EMBODIMENTS

These and other objects of the present disclosure can be achieved by provision of an exemplary apparatus that can include a pressure applying first arrangement, a pressure regulating second arrangement configured to control a pressure applied by the first arrangement, a pulse detecting third arrangement, and a hardware fourth arrangement configured control the second arrangement based on information or a signal(s) provided from the third arrangement. The second arrangement can include an air pump(s) and a solenoid valve(s). The solenoid valve(s) can be a normally open solenoid valve.

In some exemplary embodiments of the present disclosure, the third arrangement can include a pulse sensor(s), which can include an infrared emitter(s) and an infrared detector(s). The one pulse sensor(s) can also include an auscultatory arrangement(s). A light-emitting diode arrangement(s) can be configured to provide feedback from the pressure sensitive tourniquet, which can include information regarding an error with the apparatus or that the apparatus is currently being operated. The first arrangement can include an inflatable cuff.

These and other objects of the present disclosure can be achieved by provision of systems, methods and computer-accessible mediums that can, for example, receive information related to a detection of a pulse of a patient(s), and increase a pressure using a hardware arrangement to reach a first pressure level corresponding to the pulse no longer being detected. The pressure can be decreased to reach a second pressure level corresponding to the pulse being again detected, and the pressure can be maintained at the second pressure level to facilitate a venipuncture of the patient(s). The first pressure level can correspond to an arterial systolic pressure of the patient(s), and the second pressure level can correspond to a pressure that can be less than the arterial systolic pressure and greater than an arterial diastolic pressure. The information can be generated using a pulse detecting arrangement, which can be a pulse sensor or an auscultatory arrangement. The hardware arrangement can include an air pump(s) and a solenoid valve(s).

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which.

Figure 1:
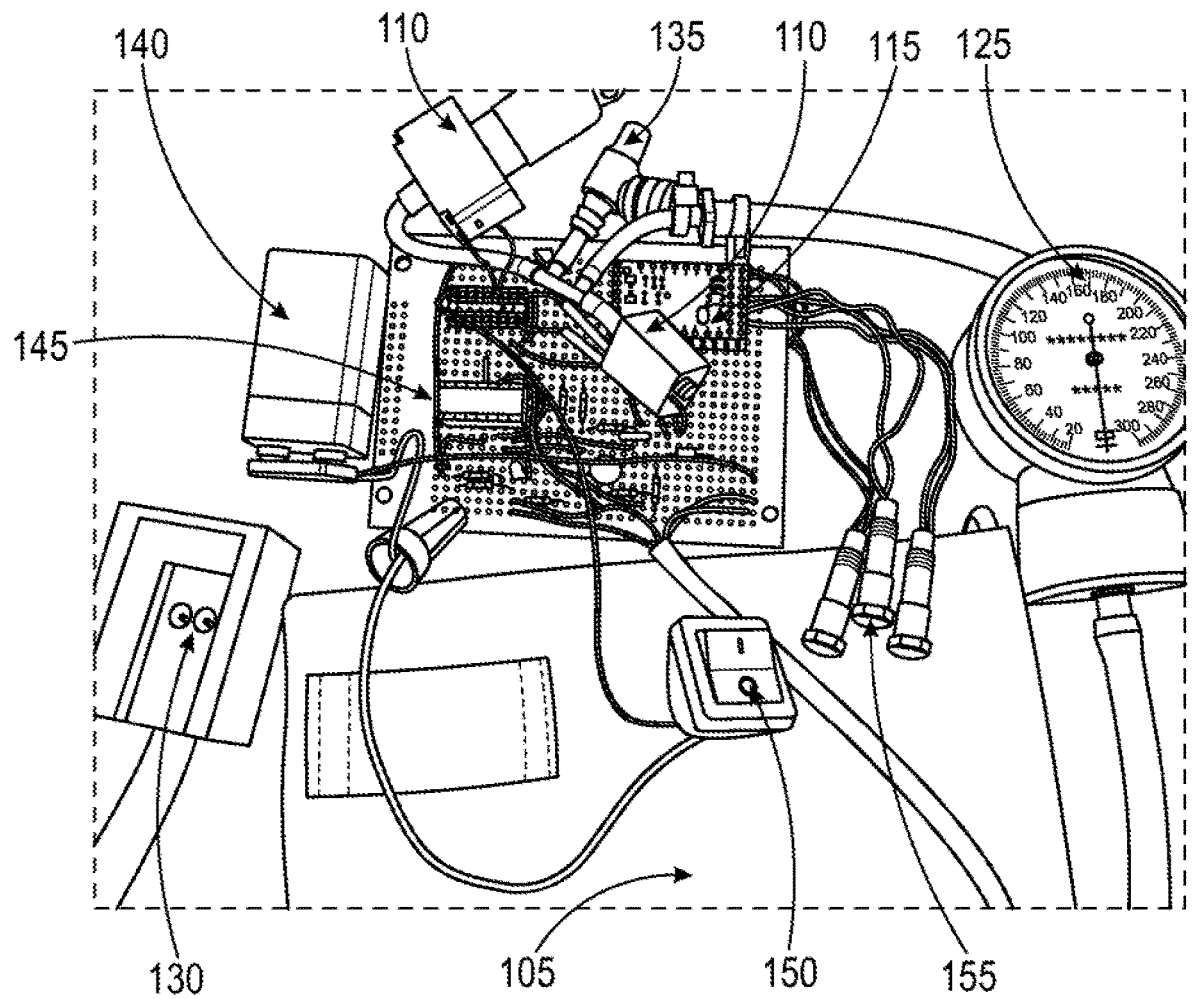
FIG. 1 is a photograph of exemplary components for the exemplary device according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

The "systolic" blood pressure is the peak arterial pressure occurring during contraction of the left ventricle of the heart. The "diastolic" blood pressure is the minimum arterial pressure which occurs during relaxation and dilatation of the ventricles of the heart as the ventricles fill with blood. The arterial diastolic pressure can approximate the pressure found in the venous circulation. The exemplary device can facilitate the optimization of tourniquet pressure between arterial systolic and diastolic pressures. The exemplary tourniquet (e.g., blood pressure cuff) can be placed on the extremity and a pulse detecting arrangement can be placed distal to the cuff. The cuff can be inflated until the pulse oximeter signal can be lost, indicating that the cuff can be inflated to the arterial systolic pressure. The cuff can be deflated until the pulse oximeter signal can be present, and then the cuff pressure can be held at this point, which can be between the arterial systolic and the diastolic pressures. This can lead to progressive and rapid venous distension, which can facilitate a superior venipuncture.

The exemplary device/apparatus can be designed and/or sized for different patient types (e.g., adult, pediatric, geriatric patients and/or obese patients), and can include an inflatable cuff 105 (e.g., a blood pressure cuff) in order to apply pressure at a patient's limb where venous distension can be created by blocking venous flow, and can facilitate arterial flow. The inflatable cuff can be an adult-sized standard blood pressure cuff.

As shown in FIG. 1, the exemplary device can include a pressure regulating unit/device/apparatus/system/arrangement, which can comprise a digital or analog circuit, as well as an air pump 110 (e.g., a miniature air pump) and a solenoid valve 115 (e.g., a normally open solenoid valve) and can be controlled by a microcontroller unit 120 ("MCU") (e.g., an Arduino controller), in order to maintain the pressure applied by the cuff 105, by determining the pressure through pressure gauge. The pressure regulating unit/device/apparatus/system/arrangement can increase, decrease or maintain the pressure at the cuff 105 by operating the solenoid valve 115 and the air pump 110. The normally-open solenoid valve 115 can be and/or include an electromagnetic component that can close the airway when electrified. The exemplary valve 115 can be used to control the release of air from the cuff 105 (e.g., deflation). The one-way valve can be, and/or can include, a mechanical component that, for example, may only facilitate the inflow of air to the cuff 105. Both the air pump 110 and the one-way valve 115 can control the inflation of the cuff 105. Table 1 below summarizes an exemplary pressure regulation by the solenoid valve and the air pump.

TABLE 1

Cuff Pressure Regulation by the Solenoid Valve and the Air Pump

| Pressure Regulation | Solenoid Valve | Air Pump |
|---|---|---|
| Increase Pressure | Close | On |
| Decrease Pressure | Open | Off |
| Maintain Pressure | Close | Off |

Figure 3:
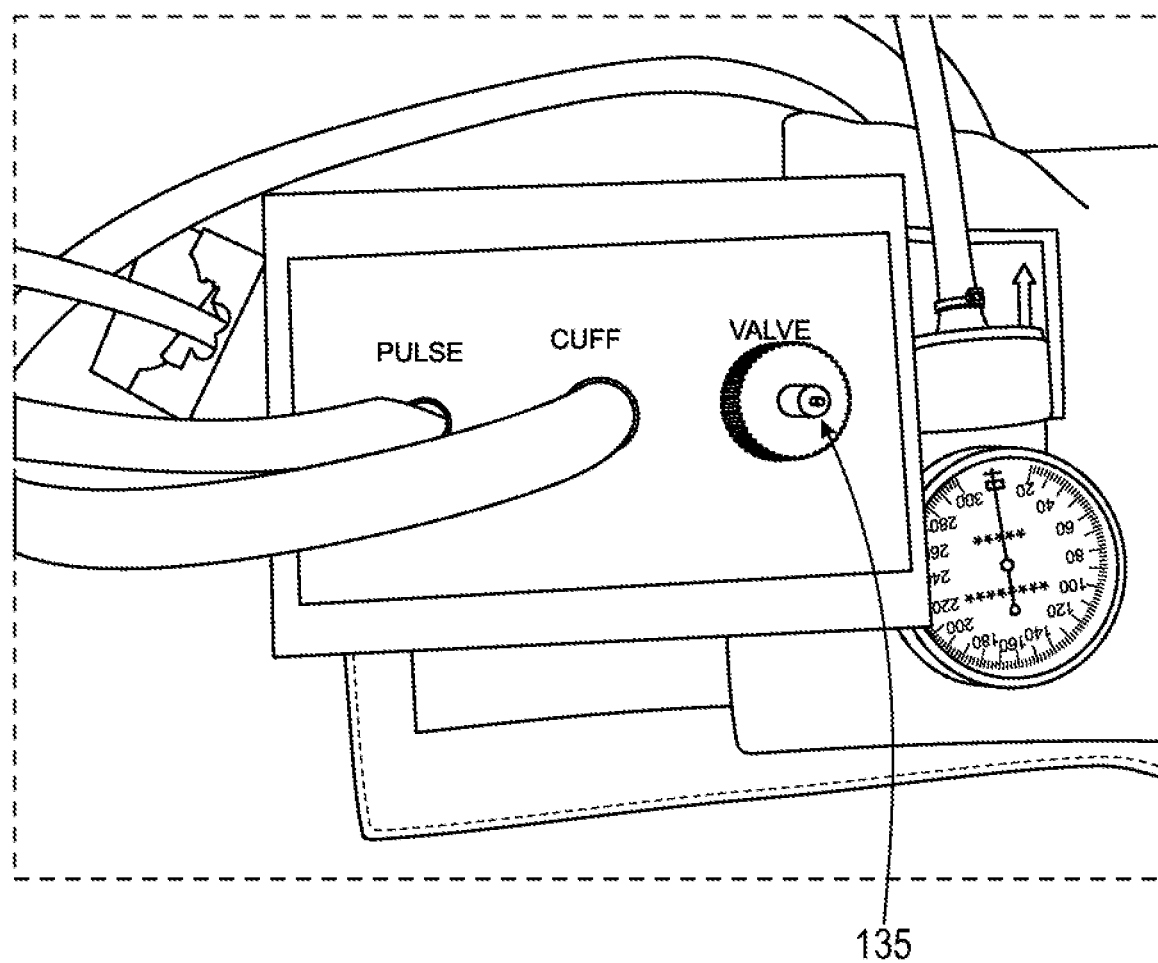
FIG. 3 is a photograph of an exemplary emergency release valve according to an exemplary embodiment of the present disclosure.

The exemplary pressure regulating unit/device/apparatus/system/arrangement can include a pulse detecting unit/apparatus 130 (e.g., an infrared emitter and detector), which can detect the patient's pulse and, can provide feedback to the pressure regulating unit. The pulse detecting unit/apparatus can be coupled to an operational amplifier (e.g., op amp 145) for processing the signal. The exemplary pressure regulating unit/device/apparatus/system/arrangement can automatically determine, apply, and/or maintain pressure between the systolic and diastolic blood pressure in order to cause venous distention (e.g., by blocking venous flow while facilitating arterial flow). The exemplary cuff 105 can be easily encircled around, and detached from, the patient's limb in order to shorten the procedure duration for each venipuncture. The exemplary pressure regulating unit/device/apparatus/system/arrangement can also include an emergency pressure release mechanism 135 (e.g., a pressure release valve) in order to avoid injury to the patient. (See, e.g., FIG. 3). Additionally, the exemplary pressure regulating unit/device/apparatus/system/arrangement can include a pressure release valve which can automatically release pressure above a predetermined amount. The applied pressure can be determined using an exemplary pressure sensor, which can initiate the release of the pressure through the pressure release valve when the predetermined amount of pressure is achieved or exceeded.

The exemplary air pump and solenoid valve can be powered by power source 140 (e.g., a battery, such as a 9V), and can be turned on and off by switch 150. A lighting apparatus 155 (e.g., light-emitting diodes ("LEDs")) can be included to indicate the operational status of the exemplary pressure regulating unit/device/apparatus/system/arrangement The exemplary pressure regulating unit/device/apparatus/system/arrangement can be lightweight (e.g., less than about 10 pounds), and can be small (e.g., 20 cm×15 cm×10 cm excluding the exemplary pulse detecting unit and the exemplary cuff). The exemplary pressure regulating unit/device/apparatus/system/arrangement can be inflatable at a rate of approximately 10-50 mmHg/sec, and can deflate at a rate of approximately 2-10 mmHg/sec.

The exemplary pulse detecting unit can include a pulse sensor (e.g., a pulse oximeter). When the pulse sensor detects blood flow, the cuff pressure can be increased above the systolic pressure, which can occlude both arterial and venous flows. The cuff pressure can be decreased to, and maintained at, a point between the systolic and diastolic pressures, where the resumption of blood flow can be detected.

The exemplary pulse detecting unit can include an auscultatory apparatus (e.g., a sound sensor). A sound sensor can be used to detect the Korotkoff sounds produced when the cuff pressure can be between the systolic and diastolic pressure by applying gradual increases in the cuff pressure. The cuff pressure can be maintained as soon as the first Korotkoff sound can be detected. The exemplary pulse detecting unit can include an oscillometric apparatus, and can apply the mean arterial pressure ("MAP"). A pressure of about 200 mmHg can be applied, which can be decreased gradually until oscillations of the artery can be detected by the pressure sensor. The pressure with the highest oscillation amplitude can be equivalent to the MAP. The pulse detecting unit can also include an indwelling arterial line.

Figure 2:
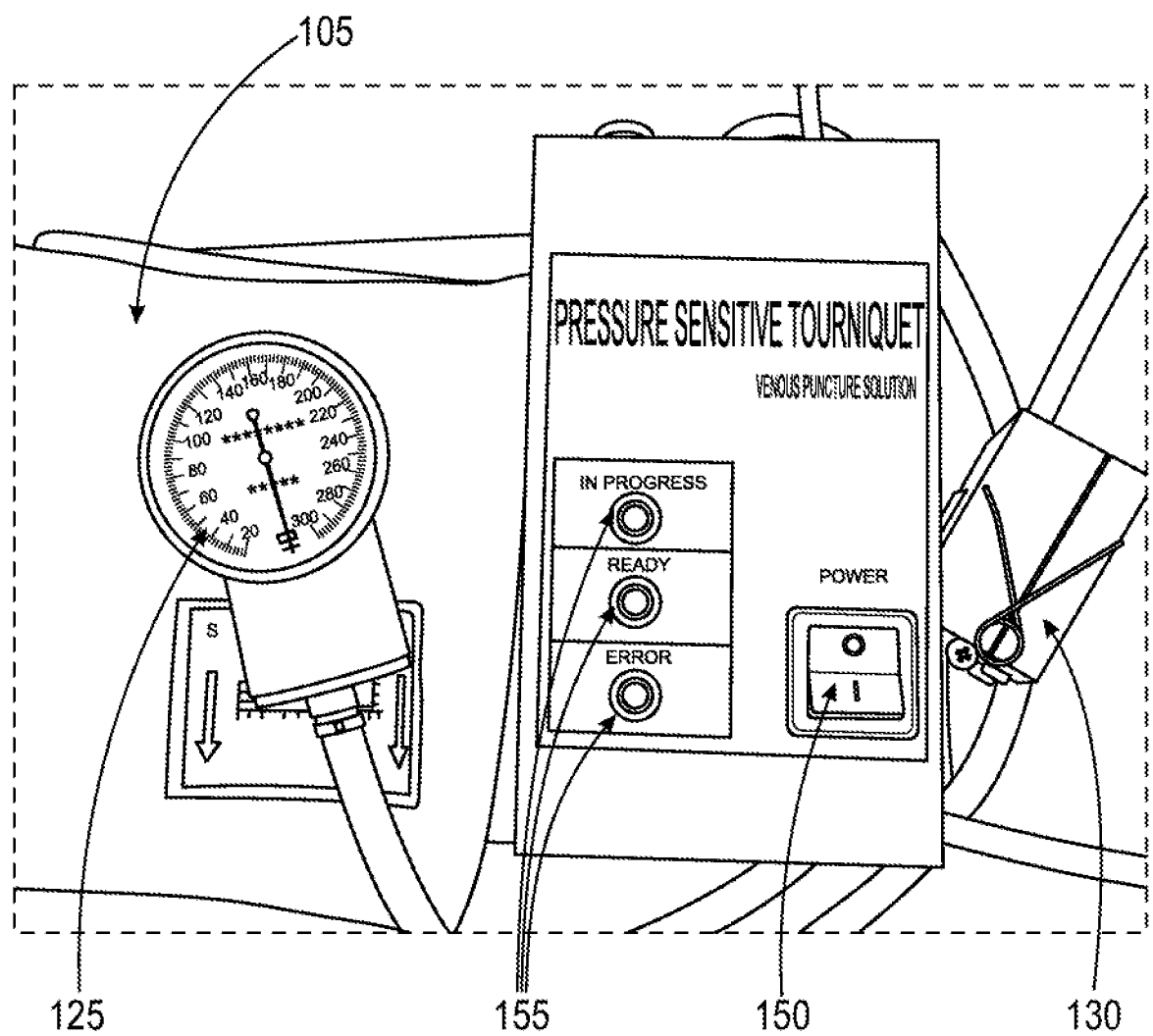
FIG. 2 is a photograph of an exemplary lighting apparatus according to an exemplary embodiment of the present disclosure.

As shown in FIG. 2, the lighting apparatus 155 can indicate the operational status of the exemplary pressure regulating unit/device/apparatus/system/arrangement. For example, three LEDs (e.g., orange, green and red) can be mounted on a top face of the exemplary pressure regulating unit/device/apparatus/system/arrangement. One or more LEDs (e.g., the orange) can signify that the device can be in operation. Another one or more LEDs (e.g., the green) can signify a successful operation of the device and thus, venipuncture can be performed. Further one or more LEDs (e.g., the red) can signify errors in device operation.

The exemplary pressure regulating unit/device/apparatus/system/arrangement can be operated by wrapping the exemplary cuff 105 around the upper arm of a patient that can be near the desired site of the venipuncture. The exemplary cuff can be tightened such that about 1-2 fingers can be inserted into the space between the patient's arm and the exemplary cuff. The exemplary sensor (e.g., pulse oximeter) can be placed on the thumb of the patient corresponding to the arm the exemplary cuff is placed on. The exemplary pressure regulating unit/device/apparatus/system/arrangement can be started and/or operated automatically.

Figure 4:
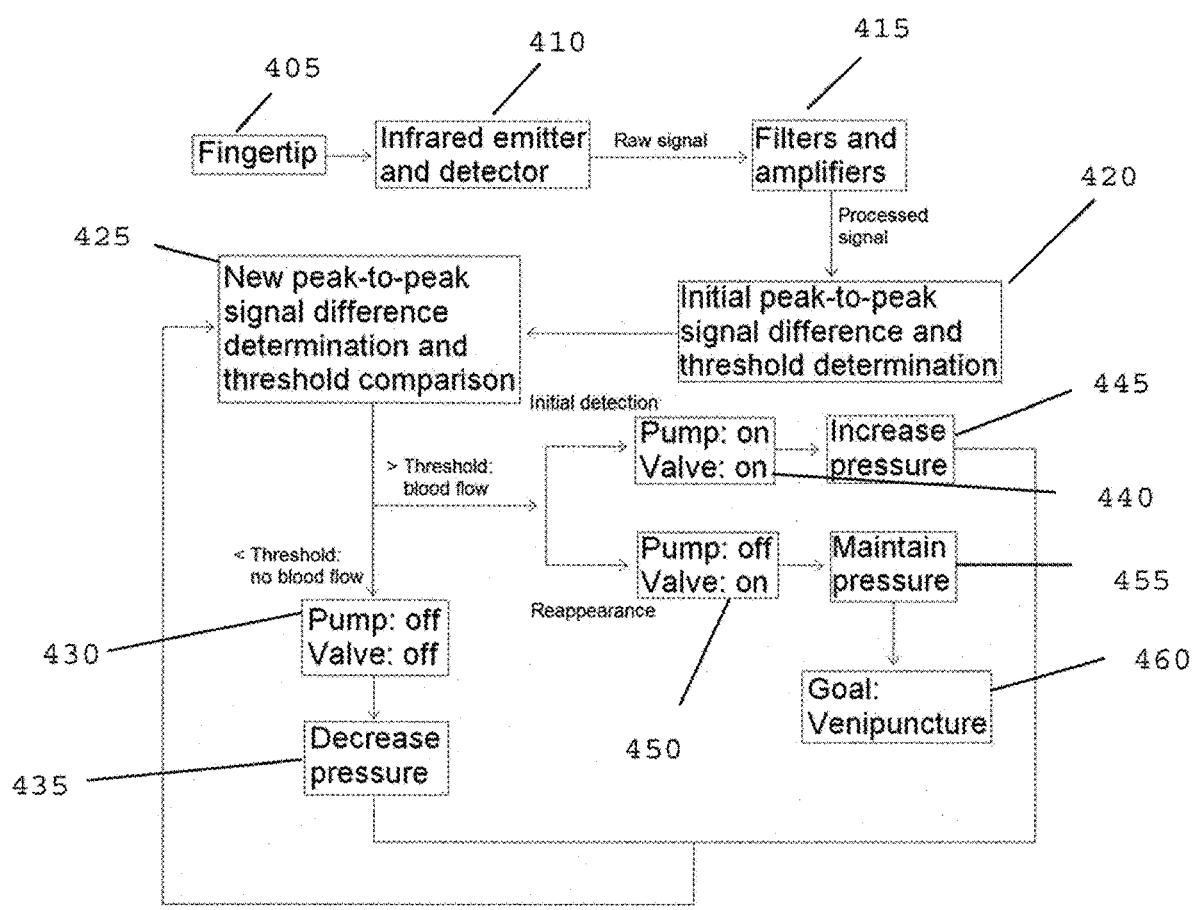
FIG. 4 is an exemplary flow diagram of a process according to an exemplary embodiment of the present disclosure.

FIG. 4 shows an exemplary flow diagram of a method for using the exemplary pressure regulating unit/device/apparatus/system/arrangement according to an exemplary embodiment of the present disclosure. For example, at procedure 410, an infrared emitter can emit a signal in a fingertip 405 and detect a signal from fingertip 405. At procedure 415, exemplary filters and amplifiers can receive the raw signal from the infrared emitter and detector and process the signal. At procedure 420, the initial peak-to-peak signal difference and threshold can be determined, and at procedure 425, a new peak-to-peak signal difference can be determined and compared to a threshold. If the blood flow can be greater than the threshold, on a first detection by the infrared emitter and detector, the pump and valve can be turned on at procedure 440 and the pressure can be increased at procedure 445. If the blood flow can be greater than the threshold, and it is the first detection by the infrared emitter and detector, then at procedure 450, the pump can be turned off, the valve can remain on and the pressure can be maintained at procedure 455 to initiate a venipuncture at procedure 460. If the blood flow can be less than the threshold at procedure 425, then the pump and valve can be turned off at procedure 430, and the pressure can be decreased at procedure 435 until the blood flow can be greater than the threshold.

Figure 5:
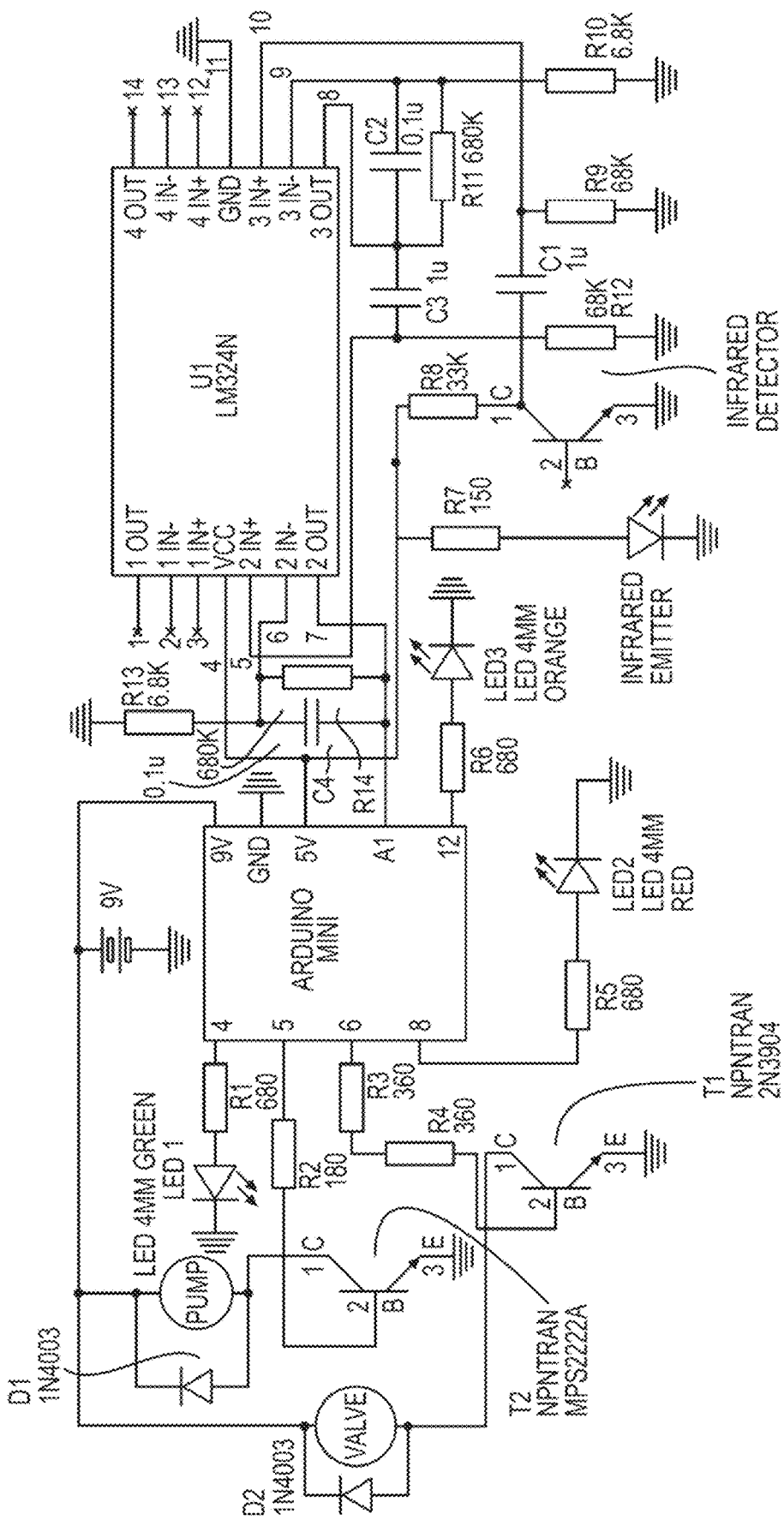
FIG. 5 is a circuit diagram of an exemplary device according to an exemplary embodiment of the present disclosure.

FIG. 5 shows an exemplary circuit diagram of the exemplary pressure regulating unit/device/apparatus/system/arrangement according to an exemplary embodiment of the present disclosure. For example, the air pump and the solenoid valve can be connected to an inflatable cuff. The resistances of the resistors and the capacitances of the capacitors are shown in Table 2. Exemplary part numbers of different components are shown in Table 3.

TABLE 2

| Resistors | Resistances (Ω) | Capacitors | Capacitance (μF) |
|---|---|---|---|
| R1, R5, & R6 | 680 | C1 & C3 | 1 |
| R2 | 180 | C2 & C4 | 0.1 |
| R3 & R4 | 360 | — | — |
| R7 | 150 | — | — |
| R8 | 33000 | — | — |
| R9 & R12 | 68000 | — | — |
| R10 & R13 | 6800 | — | — |
| R11 & R14 | 680000 | — | — |

TABLE 3

| Components | Part Numbers |
|---|---|
| Infrared Emitter and Detector | 276-142 |
| Air Pump | KPM14A-3A2 |
| Solenoid Valve | KSV05A |
| Inflatable Cuff | 143401 |
| Green 4 mm LED (LED 1) | 276-271 |
| Red 4 mm LED (LED 2) | 276-270A |
| Orange 4 mm LED (LED 3) | 276-270B |
| Transistor T1 | 2N3904 |
| Transistor T2 | MPS2222A |
| Diodes D1-D2 | 1N4003 |
| Switch | 275-695 |
| Arduino Mini 05 | A000087 |
| Operational Amplifier U1 | LM324N |

Exemplary Photoplethysmogram Signal Analysis

The exemplary pressure regulating unit/device/apparatus/system/arrangement can use a reflective photoplethysmogram ("PPG") sensor for pulse determination. The exemplary PPG sensor can detect the level of hemoglobin, which can be converted to current. Beer-Lambert's Law, absorbance and illuminance can be the principle equations used by the PPG sensor, which states that the absorbance of light can increase linearly with the concentration of the absorbing substance and the distance of the source of light. Thus, for example:

$$A = abc \tag{1}$$

which can indicate the parameters in the Beer-Lambert's Law, where A can be absorbance, a can be the molar extinction coefficient, b can be the path length, and c can be concentration.

For the exemplary PPG sensor, the exemplary path length can be constant, and can be equal to the depth of the fingertip the sensor is attached to. The absorbance can vary in relation to the concentration of the hemoglobin as the molar extinction coefficient of hemoglobin can also be a constant. Even though whole blood does not strictly follow the law (see, e.g., Reference 1), Beer-Lambert's Law can generally be valid when applied to hemoglobin at the fingertip, since red blood cells can pass one at a time through the capillary.

Absorbance can be calculated using the following exemplary equation:

$$A = \log_{10} \frac{I_{incident}}{I_{transmitted}} \tag{2}$$

where $I_{transmitted}$ can be the luminous intensity of the transmitted light and $I_{incident}$ can be the luminous intensity of the incident light.

Since the exemplary PPG sensor can be used to measure the reflected light, and the fingertip can be sealed, it can be assumed that lights can either be reflected or absorbed, thus, equation 2 can take the form of, for example:

$$A = \log_{10} \frac{I_{incident}}{I_{reflected}} \tag{3}$$

where $I_{reflected}$ can be the luminous intensity of the reflected light.

The exemplary PPG sensor can use a photodiode to produce current based on the reflected light. The current can be produced according to the following exemplary equation:

$$I = RE_v \tag{4}$$

where I can be the current, R can be the responsivity of the photodiode, and $E_v$ can be the illuminance of the light. The illuminance $E_v$ in Equation 4 can be related to the luminous intensity $I_v$ by the following exemplary equation:

$$E_v = \frac{\phi_v}{A} \frac{I_v \Omega}{A} \quad (5)$$

where $\phi_v$ can be luminous flux defined as $I_v\Omega$, $\Omega$ can be a solid angle, which can be a two-dimensional angle that can have a magnitude as the area of a piece of a unit sphere (see, e.g., Reference 2), and A can be the area the light shines to. By combining Equations 4 and 5, the output current of the photodiode can be obtained as a function of luminous intensity of the reflected light, which can be, for example:

$$I = \frac{R\Omega}{A} I_{reflected} \quad (6)$$

Exemplary Hemoglobin Concentration—Output Current Relation

Equation 1 relates concentration to absorbance, Equation 3 relates absorbance to luminous intensity and Equation 6 relates luminous intensity to current. By combining these three equations, the current can be obtained as a function of concentration, which can be, for example:

$$I = \frac{R\Omega I_{incident}}{A} 10^{-abc} \quad (7)$$

In Equation 7, R and $I_{incident}$ can be the intrinsic properties of the infrared detector and emitter. A and $\Omega$ can approximately be the projected area and the surface area of the emitter. The constants a and b can depend on the thickness of the fingertip, and absorbance of hemoglobin at the wavelength of the emitter. The hemoglobin concentration, c, can be a variable depending on blood flow of the subject. Thus, the output current of the exemplary PPG sensor can vary with the hemoglobin concentration at the fingertip. When blood flow can be occluded, hemoglobin concentration c can remain constant, so a constant current can be obtained. By differentiating a time-varying current from constant current, occlusion of blood vessels can be determined.

Exemplary Circuit Analysis

Exemplary circuit analyses can be performed using Ohm's Law on the three exemplary LEDs, the exemplary air pump and the exemplary solenoid valve. Ohm's Law relates current and resistance to voltage, as shown in the following exemplary equation:

$$V = IR \quad (8)$$

where V can be voltage, I can be current, and R can be resistance.

Exemplary LED Currents

Figure 6:
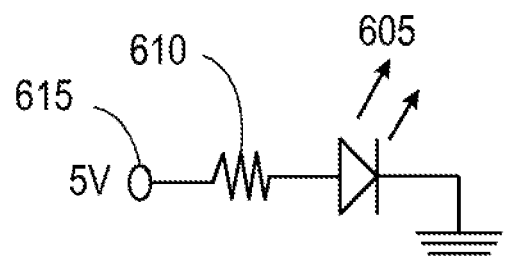
FIG. 6 is a schematic diagram of an exemplary light-emitting diode incorporated into the exemplary device according to an exemplary embodiment of the present disclosure.

Three LEDs can be used in the exemplary device/apparatus for indication purposes. An exemplary LED circuit is shown in FIG. 6. In this exemplary circuit, the LED 605 can be connected in series with a resistor 610. The power can be supplied to the circuit by the Arduino's output, which can be a constant 5 V signal 615. Since the LED and the resistor can be in series, the current in the two components can be the same. When illuminated, there can be a voltage drop across the LED. This voltage drop can be approximately 2 V. Thus, the voltage across the resistor can be the Arduino's output subtracted by 2 V. Using Ohm's Law and the resistances for R1, R5, and R6 (e.g., Table 2), the currents $I_1$, $I_2$, and $I_3$ in LED1, LED2, and LED3, respectively can be obtained as, for example:

$$I_1 = I_2 = I_3 = \frac{(5-2)V}{R1} = \frac{(5-2)V}{R5} = \frac{(5-2)V}{R6} = \frac{3\,V}{680\Omega} \approx 0.00441\,A = 4.41\,mA$$

The exemplary maximum current the LED can operate safely can be about 20 mA. (See, e.g., Reference 3). As the values of $I_1$, $I_2$, and $I_3$ can be lower than the maximum current, it can be concluded that the LED's are working safely.

Exemplary Transistors

Figure 7:
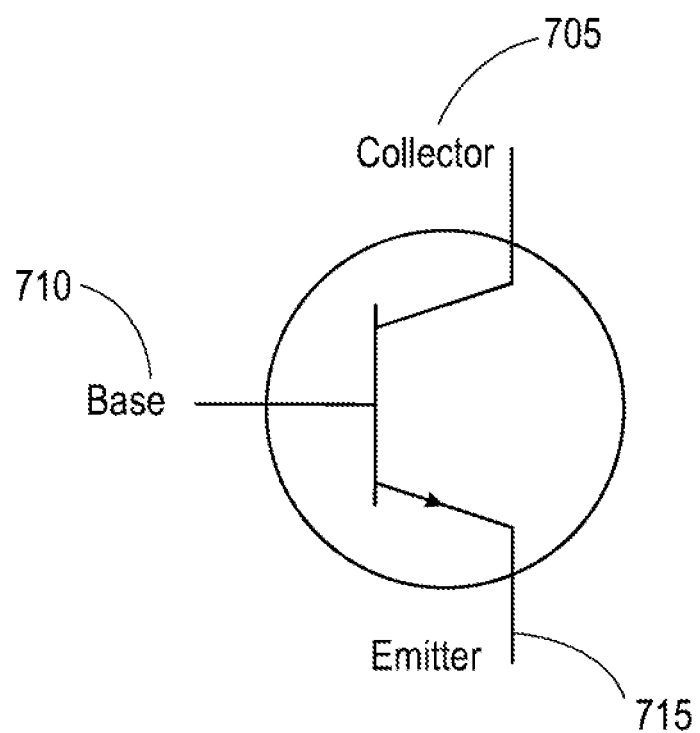
FIG. 7 is an schematic diagram of a pinout of an NPN transistor according to an exemplary embodiment of the present disclosure.

Two or more NPN transistors can be used. NPN transistors can have three pins, collector 705 ("C"), base 710 ("B"), and emitter 715 ("E"), as shown in FIG. 7. Current can flow from C to E depending on the input of B. For a NPN transistor, the current that flows into C ($I_c$) can be the amplified version of the current that flows into B ($I_b$). The DC current gain, $h_{FE}$, can be defined as the ratio of $I_c$ over $I_b$ (See, e.g., Reference 4). The $h_{FE}$ can signify a linear relationship between the input current $I_b$ and output current $I_c$.

The transistors in the exemplary pressure regulating unit/device/apparatus/system/arrangement can be used to control the air pump and the solenoid valve, as both components can utilize a large amount of current that cannot be obtained from the Arduino alone. The exemplary transistors can be configured as switches that can control the air pump and the solenoid valve based on $I_b$. Switching transistors may need saturation, as only two states—"on" and "off" can exist for saturated transistors. (See, e.g., Reference 6). Saturation in a transistor can usually be done by inputting large $I_b$ such that $I_c$ becomes independent of the gain. Thus, $I_c$ can remain constant as long as $I_b$ may not be zero (e.g., On), and $I_c$ can become zero when $I_b$ can be zero (e.g., Off). The transistor can be saturated when $I_b$ can be approximately of $$\frac{1}{10}I_c.$$

Figure 8:
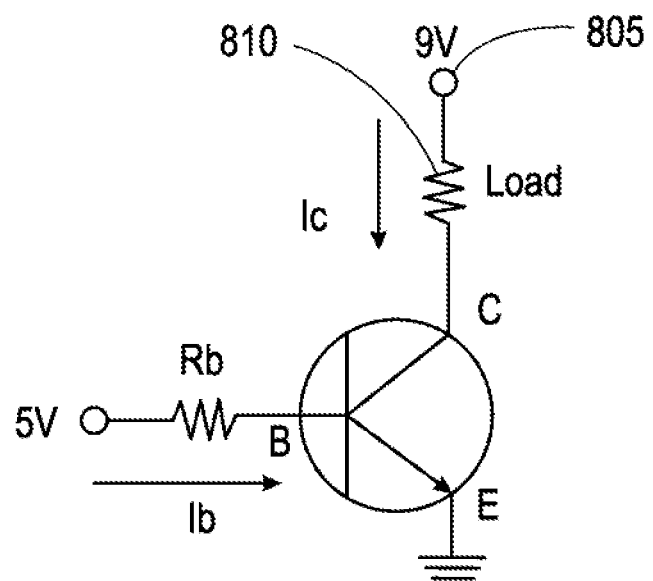
FIG. 8 is a schematic diagram of an exemplary circuit used in the exemplary device according to an exemplary embodiment of the present disclosure.

The exemplary air pump and solenoid valve can be powered by a 9V battery 805, and can be connected according to the transistor circuit shown in FIG. 8. The operating currents of the air pump and the solenoid valve can be about 380 mA and about 75 mA, respectively, when the power supply can be capable for outputting these currents. (See, e.g., References 7 and 8). Thus, by modeling the air pump and solenoid valve as load resistors 810, the corresponding $I_c$ values of the air pump and solenoid valve can be equal to the operating currents. The current $I_b$ can then be determined and can consequently be $R_b$.

Exemplary Air Pump and Solenoid Valve

To saturate transistors T1 and T2, $I_b$ can be chosen as about 28 mA and about 7 mA, for the air pump and the solenoid valve, respectively. Using Ohm's Law (e.g., Equation 8), the resistances of the resistors connecting to pin B ($R_b$) can be determined as, for example:

$$R_b = \frac{5 \text{ V}}{0.028 \text{ A}} \approx 180 \text{ }\Omega \quad \text{(AirPump)}$$

$$R_b = \frac{5 \text{ V}}{0.007 \text{ A}} \approx 720 \text{ }\Omega \quad \text{(Solenoid Valve)}$$

Thus, an approximately 180Ω resistor (e.g., R2) can be connected to pin B of transistor T2 for the air pump (see e.g., Table 2 and FIG. 5). An approximately 720Ω resistance can be achieved by connecting two approximately 360Ω resistors (e.g., R3 & R4) in series for the solenoid valve. (i.d.).

Induced Voltage Estimation

The air pump and the solenoid valve can be electromechanical components that contain solenoids (e.g., coils). Solenoids can induce electromotive force ("EMF"), or voltage, when magnetic flux through the solenoid changes with time. This is known as Faraday's Law. Faraday's Law can be shown in the following exemplary formula (see, e.g., Reference 9):

$$\varepsilon = -N\frac{d\phi_B}{dt} \quad (9)$$

where ε can be the induced voltage EMF, N can be the number of loops, $$\frac{d\phi_B}{dt}$$

can be the derivative of magnetic flux ($\phi_B$) with respect to time (t).

Magnetic flux in Equation 9 can be defined as the surface integral of the dot product of magnetic field, and the normal vector to an area where magnetic field lines pass through. (See, e.g., FIG. 9). Magnetic flux can be calculated using exemplary Equation 10. (See, e.g., Reference 10).

$$\phi_B = \oint \vec{B} \cdot d\vec{A} = AB\cos(\theta) \quad (10)$$

where $\vec{B}$ can be magnetic field with magnitude B, $\vec{A}$ can be the normal vector of the area magnetic field lines pass through with area A, and θ can be the smallest angle between the two vectors.

Figure 9:
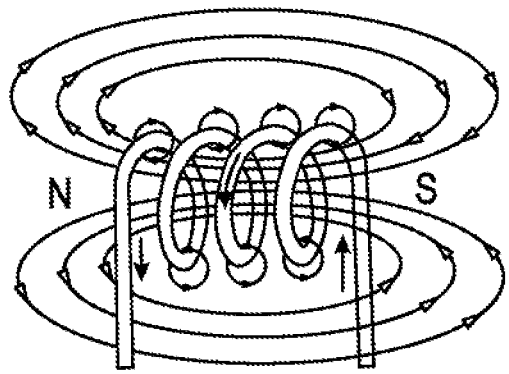
FIG. 9 is an illustration of an exemplary magnetic field produced by an exemplary solenoid used in the exemplary device according to an exemplary embodiment of the present disclosure.

As shown in FIG. 9, the solenoid can produce magnetic fields based on the current. The Magnetic field produced by the solenoid can be calculated using Equation 11 (see, e.g., Reference 11), where, for example:

$$B = -\mu_0 \frac{N}{l} I \quad (11)$$

where $\mu_O$ can be the permeability of free space, l can be the length of the solenoid, and I can be the current in the solenoid.

Since the magnetic field produced inside of the solenoid can be parallel to the normal vector of the cross-sectional area of the solenoid (see, e.g., FIG. 5), the surface integral and dot product in Equation 10 can be simplified to exemplary Equation 12 (cos(0°)=1).

$$\phi_B = BA \quad (12)$$

Combining Equations 9, 11 and 12, an expression for induced voltage due to the change of current in the solenoid can be obtained as, for example:

$$\varepsilon = -A\mu_0 \frac{N^2}{l} \frac{dI}{dt} \quad (13)$$

Figure 10:
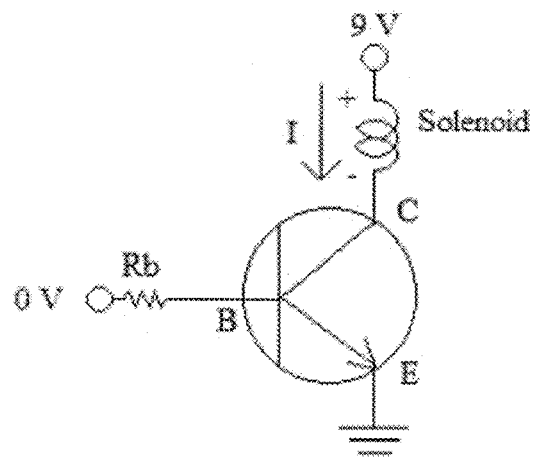
FIG. 10 is an exemplary circuit diagram illustrating current produced by the exemplary device according to an exemplary embodiment of the present disclosure.
Figure 11:
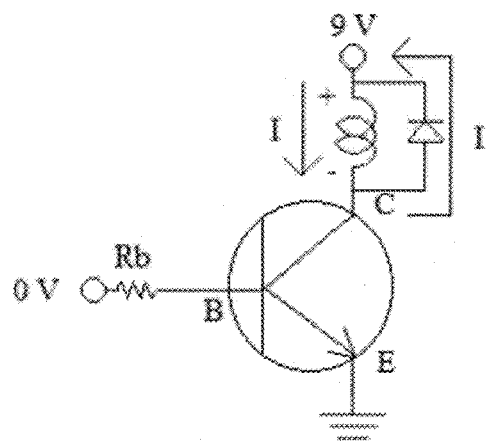
FIG. 11 is an exemplary circuit diagram illustrating current redirection by the exemplary device according to an exemplary embodiment of the present disclosure.

Equation 13 can relate the change of current to the voltage induced by the solenoid. The term $$A\mu_0 \frac{N^2}{l}$$

can be known as the inductance of the solenoid. According to this formula, when the air pump and the solenoid valve can be turned off, the current can suddenly decrease to zero. A sudden decrease in current $$\left(\frac{dI}{dt} < 0\right)$$

can induce a positive EMF (ε) with respect to the ground as shown in FIG. 10. These exemplary induced voltages, together with the 9V battery, can produce large currents toward the transistors, can enter the ground pin of the Arduino, and can damage the two components. FIG. 11 illustrates an exemplary circuit diagram of the exemplary current redirection by the exemplary pressure regulating unit/device/apparatus/system/arrangement.

Exemplary Protective Diode

One solution to avoid the potential damage of the prototype due to the induced voltages can be to connect a diode parallel to the exemplary solenoid (see, e.g., Reference 13) (e.g., air pump and solenoid valve) as shown in FIG. 7. The diodes (e.g., D1 and D2 shown in FIG. 5) connected across the solenoid valve and the air pump can be termed protective diodes and can complete the short circuits that redirect the induced currents back to the solenoids, thus preventing damage to the rests of the circuitry.

Exemplary Air Pump Flow Rate and Applied Pressure Estimation

The exemplary pressure regulating unit/device/apparatus/system/arrangement can be used to apply pressure to the patient's arm through inflation of the inflatable cuff by air. By assuming air as an ideal gas, the cuff pressure can be predicted using the ideal gas law, which can be, for example:

$$PV = nRT \quad (14)$$

where P can be the absolute pressure, V can be the volume, n can be the number of molecules, R can be the gas constant, and T can be the absolute temperature.

While encircling a patient's arm, the inflatable cuff can only hold a specific volume. When this volume can be reached, the number of molecules can increase due to the input of air by the pump while the volume remains unchanged. If the air pump's volumetric flow rate can be Q, the gauge pressure of the inflatable cuff, P, can be calculated using the following exemplary formula derived from the ideal gas law:

$$P = RT\left(\rho + \frac{Qpt}{v}\right) + P_L - P_{atm} \quad (15)$$

where ρ can be the density of air, $$\frac{n}{v},$$

Q can be the volumetric flow rate, $P_L$ can be the load pressure, and $P_{atm}$ can be the atmospheric pressure.

The term $Q\rho t$ in Equation 15 can be the number of molecules pumped into the inflatable cuff in time t due to volumetric flow rate of Q (e.g., $Q\rho$ can be molar flow rate of air). $P_L$ can be the load pressure defined as the pressure that the air pump operates against. It can also be that the pressure remains in the cuff due to the previous pumping. Because the pressure in the ideal gas law can be the absolute pressure, atmospheric pressure $P_{atm}$ can be subtracted to obtain the applied pressure, which can be a gauge pressure. Since air can be assumed to be an ideal gas, the term $RT\rho$ can be the same as atmospheric pressure, and the two terms can cancel out. Equation 15 can then be simplified to, for example:

$$P = \frac{RT\rho}{V}(Qt) + P_L \tag{16}$$

If the volumetric flow rate Q of the air pump can be known, the applied pressure can be calculated or otherwise determined using Equation 16. However, the volumetric flow rate can be a function of load pressure $P_L$.

Exemplary Air Volumetric Flow Rate

The exemplary air pump can have a volumetric flow rate curve under the zero-load current of 155 mA. (See, e.g., Reference 8). This curve can follow a typical exponential decay and can be approximated by the following exemplary equation:

$$Q = 1.33 * 10^{-5} * e^{-0.0046 P_L} \tag{17}$$

In the exemplary device, the zero-load current can be about 380 mA. If it can further be assumed that the volumetric flow rate curve can maintain its shape, but the magnitude can change linearly with the zero-load current, the volumetric flow rate for 380 mA can be obtained as, for example:

$$Q = 3.27 * 10^{-5} * e^{-0.0046 P_L} \tag{18}$$

Figures 12, 13:
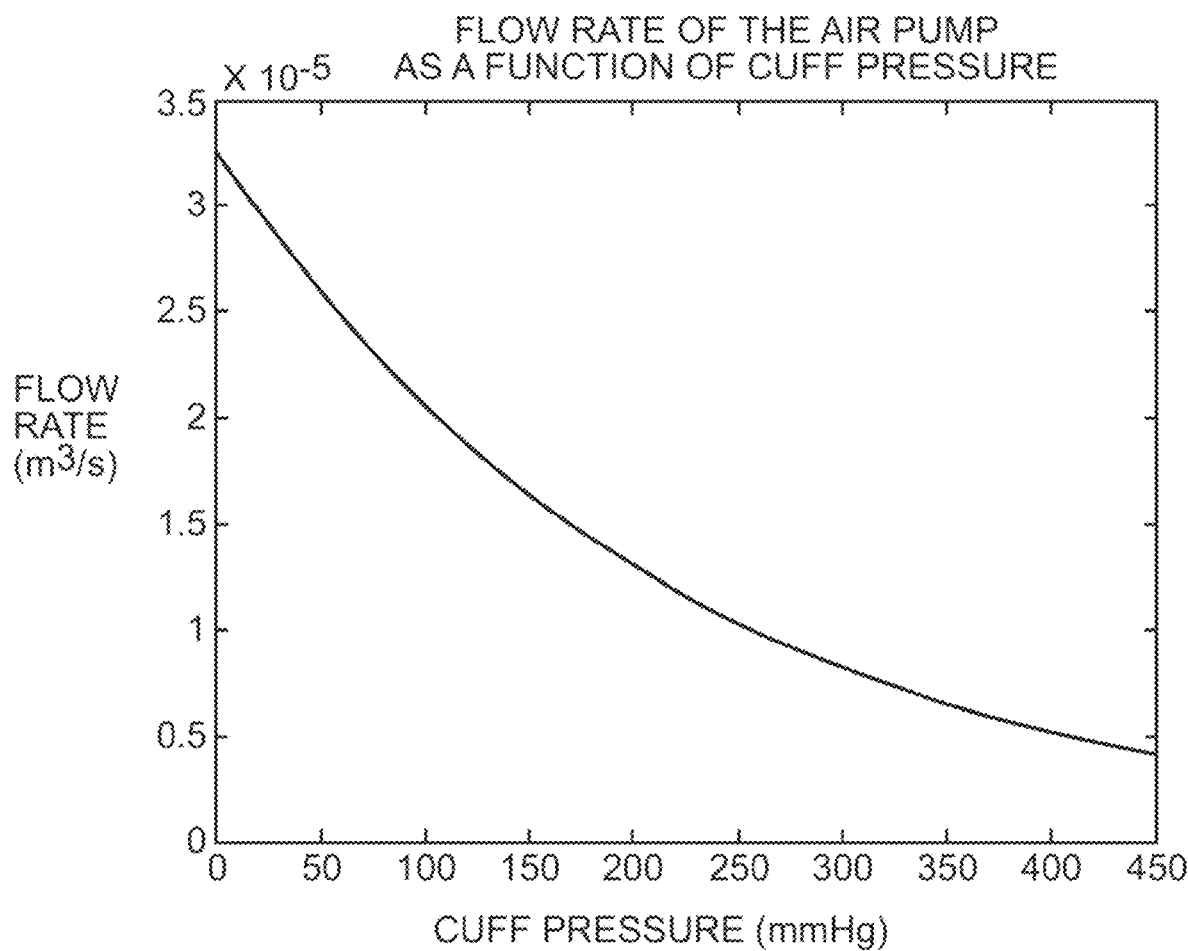
FIG. 12 is an exemplary graph illustrating an estimated volumetric flow rate curve of an exemplary pump according to an exemplary embodiment of the present disclosure.
FIG. 13 is an exemplary illustration of the conservation of mass in a control volume.

Equation 18 is plotted in FIG. 12. When the load pressure, or pressure that exists inside the cuff due to previous pumpings increases, the volumetric flow rate can decrease.

Exemplary Applied Pressure Estimation

By substituting Equations 18 into Equation 16, the applied pressure as a function of the load pressure, or the pressure existing in the cuff, can be obtained as, for example:

$$P = 3.27 * 10^{-5} * \frac{RT\rho t}{V} e^{-0.0046 P_L} + P_L \tag{19}$$

Because of the stepwise application of pressure in the exemplary device, Equation 19 can be used to estimate the newly applied pressure to the arm using the existing pressure in the cuff ($P_L$).

Exemplary Blood Flow Modeling

Blood flow through arteries and veins can be determined by utilizing the conservation of mass principle, which states that the rate of accumulation of mass in a control volume can equal the difference between the flows of mass into and the mass out of the control volume, as shown in FIG. 13.

Exemplary Poiseuille Flow

The flow of blood can be assumed to be a pressure-driven laminar flow of an incompressible Newtonian fluid (e.g., blood) through a cylindrical tube (e.g., blood vessel). Such a case can be known as the Poiseuille flow.

Figure 14A:
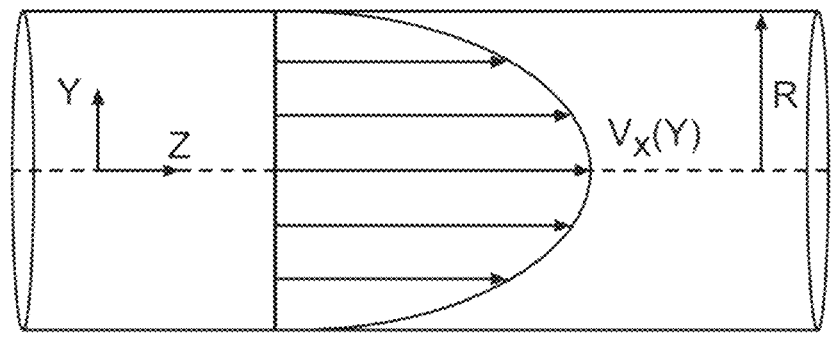
FIG. 14A is an exemplary diagram illustrating a laminar flow of a Newtonian fluid through a cylinder.
Figure 14B:
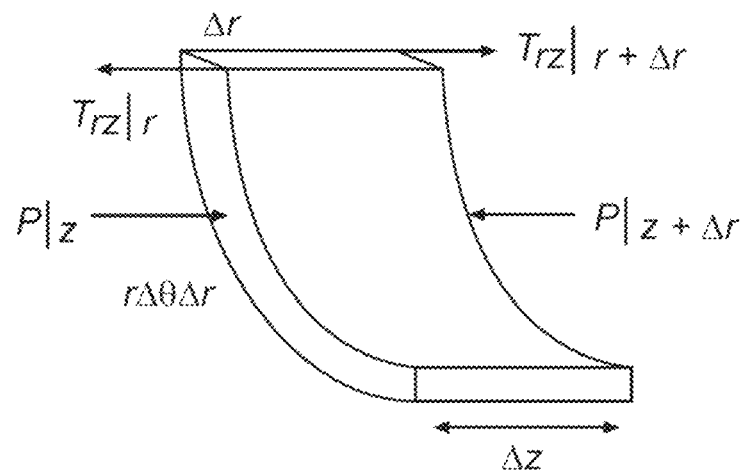
FIG. 14B is an exemplary diagram illustrating a momentum balance on a differential volume.

The flow can be unidirectional along the longitudinal axis. When it can be fully developed, the velocity of blood can be a function of radius only, and can be expected to exhibit maximum velocity with a radial symmetry about the centerline. The velocity profile under these assumptions is shown in FIGS. 14A, which illustrates laminar flow of a Newtonian fluid through a cylinder, and 14B, which illustrates a momentum balance on a differential volume.

Since the flow can be steady, the sum of all forces can be equal to zero, and the only relevant forces can be pressures and shear stresses. Under these assumptions, the Navier-Stokes Equation in the z-direction (e.g., exemplary Equation 20) can be simplified to exemplary Equation 21.

$$\rho\left(\frac{\partial V_z}{\partial t} + \frac{\partial V_z}{\partial r} + \frac{V_०}{r}\frac{\partial V_z}{\partial \theta} + V_z \frac{\partial V_z}{\partial z}\right) = \tag{20}$$
$$-\frac{dP}{dZ} + \mu\left[\frac{1}{r}\frac{d}{dr}\left(r\frac{dV_z}{dr}\right) + \frac{1}{r^2}\frac{\partial^2 V_z}{\partial \theta^2} + \frac{\partial^2 V_z}{\partial z^2}\right] + \rho g_z$$

$$0 = -\frac{dP}{dz} + \frac{\mu}{r}\frac{d}{dr}\left(r\frac{dV_z}{dr}\right) \tag{21}$$

where P can be pressure, z can be the longitudinal direction, $\mu$ can be viscosity, r can be the radial direction, and $V_z$ can be the velocity in the z-direction.

In Equation 21, pressure P can be a function of z, and velocity $V_z$ can be a function of r. The only situation where the sum of the derivatives of a function of z and a function of r can be zero is when they both can be constants. By integrating the pressure gradient as a constant with boundary conditions ("BC"), the following, for example, can be obtained:

$$P(0) = P_O \text{ and } P(L) = P_L \tag{BC:Pressure}$$

and the pressure distribution can be obtained as, for example:

$$P(z) = \frac{P_0 - P_L}{L} z + P_0 \tag{22}$$

where $P_O$ can be the pressure at the origin (e.g., the heart), L can be the distance from the origin, and $P_L$ can be the pressure at a distance L (e.g., the extremity).

By taking the derivative of Equation 22 with respect to z, and substituting the expression into Equation 21, the differential equation of $V_z$ can be obtained as, for example:

$$\frac{P_0 - P_L}{L} = \frac{\mu}{r}\frac{d}{dr}\left(r\frac{dV_z}{dr}\right) \tag{23}$$

The general solution to Equation 23 can be, for example:

$$V_z(r) = \frac{(P_0 - P_L)r^2}{4L\mu} + C_1 \ln(r) + C_2 \tag{24}$$

where $C_1$ and $C_2$ can be constants of integration.

By using the following boundary conditions, the velocity profile $V_z$ can be obtained as, for example:

$$V_2(R) = 0 \text{ and } \frac{dV_z}{dr}(0) = 0$$
(BC: Velocity)

and, for example:

$$V_z(r) = \frac{(P_0 - P_L)R^2}{4L\mu}\left(\frac{r^2}{R^2} - 1\right) \quad (25)$$

Exemplary Blood Volumetric Flow Rate

The volumetric flow rate of blood $Q_B$ (e.g., Equation 27 below) can be obtained by integrating the velocity over the cross-sectional area of the blood vessel. Thus, for example $$Q_B = \int_0^R V_z(r) 2\pi r\, dr \quad (26)$$

$$Q_B = \frac{(P_0 P_L)\pi R^4}{8L\mu} \quad (27)$$

The exemplary pressure regulating unit/device/apparatus/system/arrangement can be used to apply pressure between the systolic and diastolic pressures. The brachial artery and the cephalic vein are the two main blood vessels in the upper arm that can receive the applied pressure. The diameter of the brachial artery can be approximately 3.52 mm, (see, e.g., Reference 16), and the diameter of the cephalic vein can be about 2.4 mm. (See, e.g., Reference 17). The cephalic vein can be assumed to be occluded when the applied pressure can be higher than the diastolic pressure. The brachial artery can be assumed be occluded if the applied pressure can be higher than the systolic pressure. The radii can be described using the following exemplary equations for the brachial artery and the cephalic vein, respectively, by assuming the radii decrease linearly when the applied pressure can be increased:

$$R_A = \begin{cases} 0.00176 - \dfrac{0.00176}{SP}P, & 0 \le P \le SP \\ 0, & P > SP \end{cases} \quad (28)$$

and, for example:

$$R_V = \begin{cases} 0.0012 - \dfrac{0.0012}{DP}P, & 0 \le P \le DP \\ 0, & P > DP \end{cases} \quad (29)$$

The radii can be redefined to zero when the applied pressure can be greater than the systolic pressure, and the diastolic pressure for the brachial artery and the cephalic vein, respectively, since negative radii can be physically impossible.

The flow rate in Equation 27 can assume blood to be a Newtonian fluid. However, blood's behavior can depend on shear rate (e.g., velocity gradient). A more sophisticate model of blood flow can be shown as, for example:

$$Q_B = \frac{\pi R^4 \Delta P}{8\eta N^L}\left[1 + \frac{11}{21}\left(\frac{r_0}{r_w}\right)^4 - \frac{16}{7}\sqrt{\left(\frac{r_0}{r_w}\right)} + \frac{8}{3}\left(\frac{r_0}{r_w}\right)\right] \quad (30)$$

(see, e.g., Reference 18) where R can be radius of the blood vessel, P can be pressure, $\eta_N$ can be blood viscosity at high shear rate, L can be the length of the blood vessel, $\tau_O$ can be yield stress of blood, and $\tau_W$ can be shear stress at the wall of the blood vessel.

Exemplary Hoop Stress Analysis

Exemplary Hoop Stress

The inflatable cuff can be wrapped around the upper arm to apply a pressure. The pressure the exemplary device/apparatus can apply can be approximately 220 mmHg depending on different individuals. In the presence of an exerted pressure, the walls of blood vessels can contract. Therefore, the blood vessels can resist the contraction force with a hoop stress in the circumferential direction to avoid any vessel damage. The hoop stress can have vital physiological significance. It can be the primary force in regulating blood vessel wall thickness and residue stress, in response to blood pressure and hypertension. (See, e.g., Reference 19). Assuming that the blood vessels can be very thin, the hoop stress can be calculated using, for example:

$$\sigma_\theta = \frac{pr}{t} \quad (31)$$

(see, e.g., Reference 20) where $\sigma_\theta$ can be the hoop stress, P can be pressure, r can be radius, and t can be thickness.

Exemplary Hoop Stress Calculation

The exemplary dimensions for the brachial artery and the cephalic vein are summarized in Table 4 below. The hoop stresses can be calculated using Equation 31 at a maximum pressure of about 220 mmHg. The hoop stresses calculated from previous experimental studies are included in the table as references to determine the accuracy of the exemplary calculation.

TABLE 4

Dimensions of the Blood Vessels, Calculated Hoop Stresses and Reference Hoop Stresses.

| | Brachial Artery | Cephalic Vein |
| --- | --- | --- |
| Thickness (t) | 0.35 mm | 1.35 mm |
| Diameter (2r) | 3.52 mm | 2.40 mm |
| Radius/Thickness (r/t) | 5.03 | 0.89 |
| Calculated Hoop Stress | 147.5 kPa | 26.1 kPa |
| Reference Hoop Stress | 100 kPa-280 kPa | 245 kPa |

Exemplary Blood Vessel Damage Analysis

One of the purposes of the hoop stress analysis can be to ensure that the maximum applied pressure of about 220 mmHg does not cause any damage to blood vessels. According to one study, most human arteries' can yield hoop stresses which can be in the order of $10^5$ Pa (e.g., 100 kPa). (See, e.g., Reference 19). In another study, most mammalian arteries can be expected to exert hoop stress between about 240 kPa and about 280 kPa at about 100 mmHg. (See, e.g., Reference 23). In the exemplary analysis, the brachial artery can exert about 147.5 kPa at the maximum pressure of about 220 mmHg. Since 147.5 kPa can be in the order of about $10^5$ Pa and much less than about 240 kPa, the exemplary device does not cause any damage to the brachial artery. Similarly, the cephalic vein can be found to exert a hoop stress of about 245 kPa at the mean arterial pressure under normal physiological conditions. (See, e.g., Reference 22). In the exemplary analysis, the hoop stress for cephalic vein can be calculated to be about 26.1 kPa at the maximum pressure of about 220 mmHg. Since 26.1 kPa can be much less than about 245 kPa, the pressure exerted from the exemplary device will not damage the cephalic vein.

Figure 15:
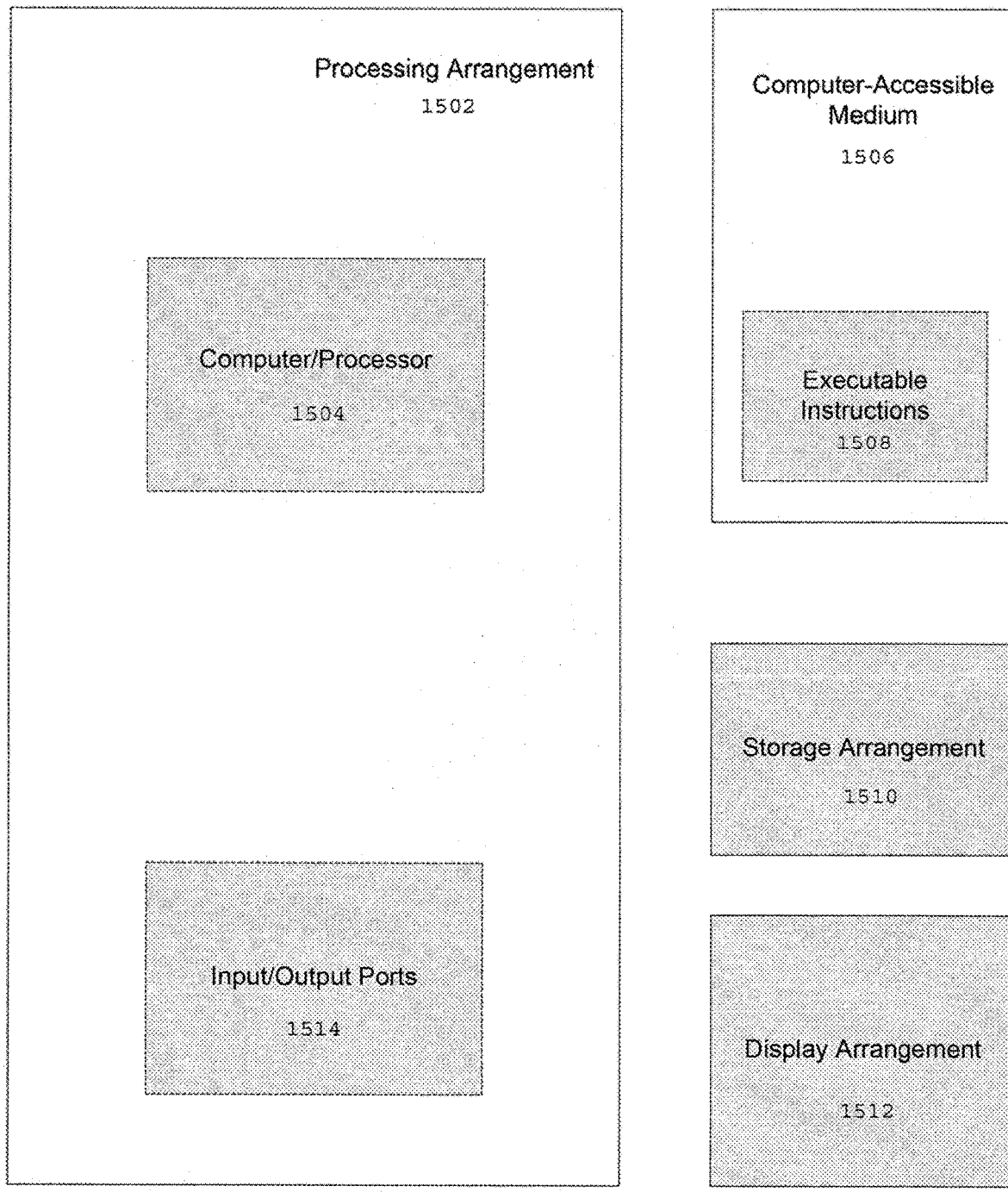
FIG. 15 is an exemplary block diagram of an exemplary system according exemplary embodiment of the present disclosure.

FIG. 15 shows a block diagram of an exemplary embodiment of a system according to the present disclosure. For example, exemplary procedures in accordance with the present disclosure described herein can be performed by a processing arrangement and/or a computing arrangement 1502. Such processing/computing arrangement 1502 can be, for example, entirely or a part of, or include, but not limited to, a computer/processor 1504 that can include, for example, one or more microprocessors, and use instructions stored on a computer-accessible medium (e.g., RAM, ROM, hard drive, or other storage device).

As shown in FIG. 15, for example, a computer-accessible medium 1506 (e.g., as described herein above, a storage device such as a hard disk, floppy disk, memory stick, CD-ROM, RAM, ROM, etc., or a collection thereof) can be provided (e.g., in communication with the processing arrangement 1502). The computer-accessible medium 1506 can contain executable instructions 1508 thereon. In addition or alternatively, a storage arrangement 1510 can be provided separately from the computer-accessible medium 1506, which can provide the instructions to the processing arrangement 1502 so as to configure the processing arrangement to execute certain exemplary procedures, processes and methods, as described herein above, for example.

Further, the exemplary processing arrangement 1502 can be provided with or include an input/output arrangement 1514, which can include, for example, a wired network, a wireless network, the Internet, an intranet, a data collection probe, a sensor, etc. As shown in FIG. 15, the exemplary processing arrangement 1502 can be in communication with an exemplary display arrangement 1512, which, according to certain exemplary embodiments of the present disclosure, can be a touch-screen configured for inputting information to the processing arrangement in addition to outputting information from the processing arrangement, for example. Further, the exemplary display 1512 and/or a storage arrangement 1510 can be used to display and/or store data in a user-accessible format and/or user-readable format.

According to further exemplary embodiments of the present disclosure, it can be possible to provide certain exemplary changes to the system according to the exemplary embodiment of the present disclosure. For example, it can be possible to utilize a standard 9V alkaline battery, although a use of a 9V lithium battery can provide an extended capacity (e.g., which can be as much as 3 times) greater than a 9V alkaline battery. In addition, for example, it can be possible to provide a configuration which can effectuate a reverse battery protection. A further exemplary solenoid valve can be provided which can have a higher voltage capacity, and which can lower power consumption. Further, instead of or together with the external release valve, it can be possible to utilize an integral release valve.

Figure 16:
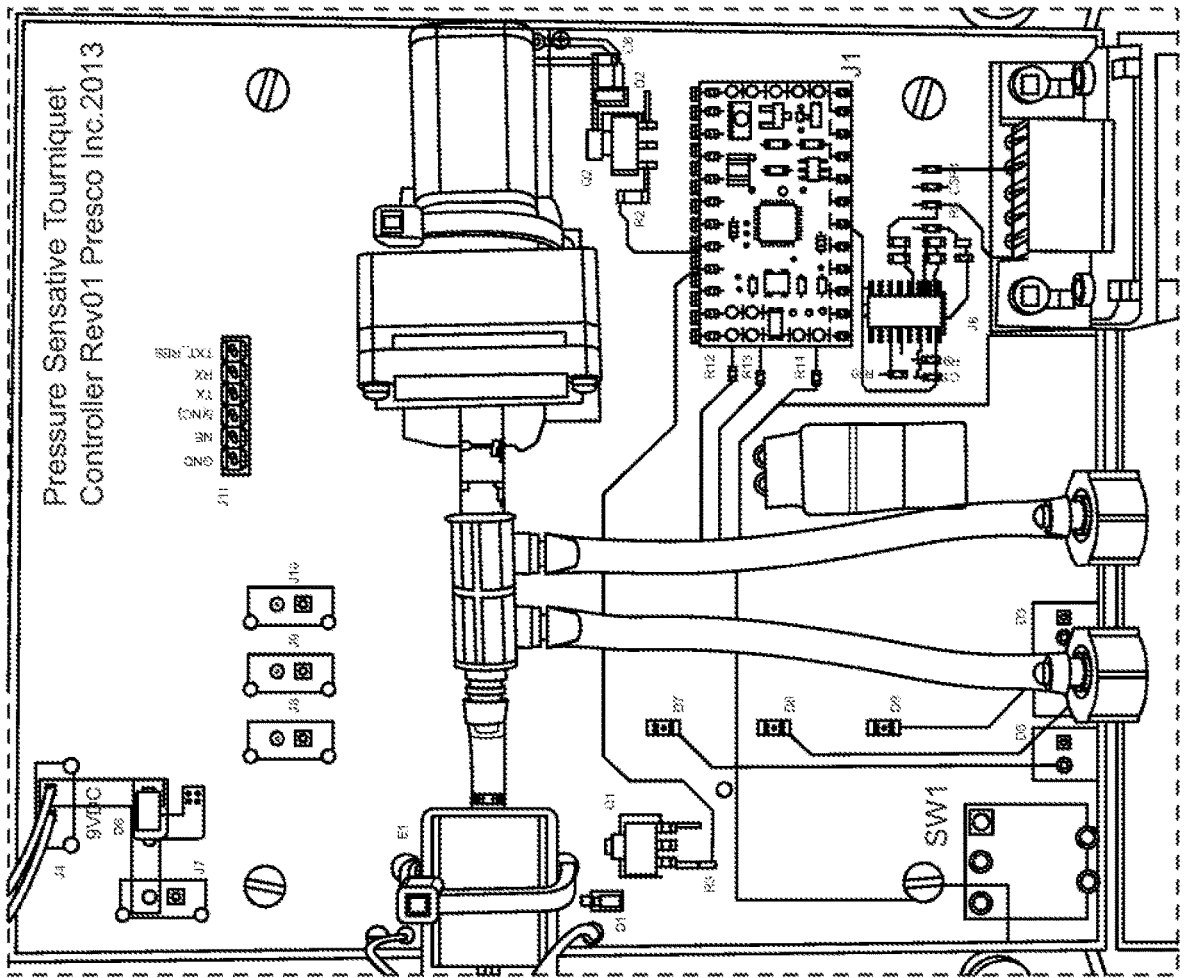
FIG. 16 is a top view photograph of an exemplary circuit board according to an exemplary embodiment of the present disclosure.
Figure 17A:
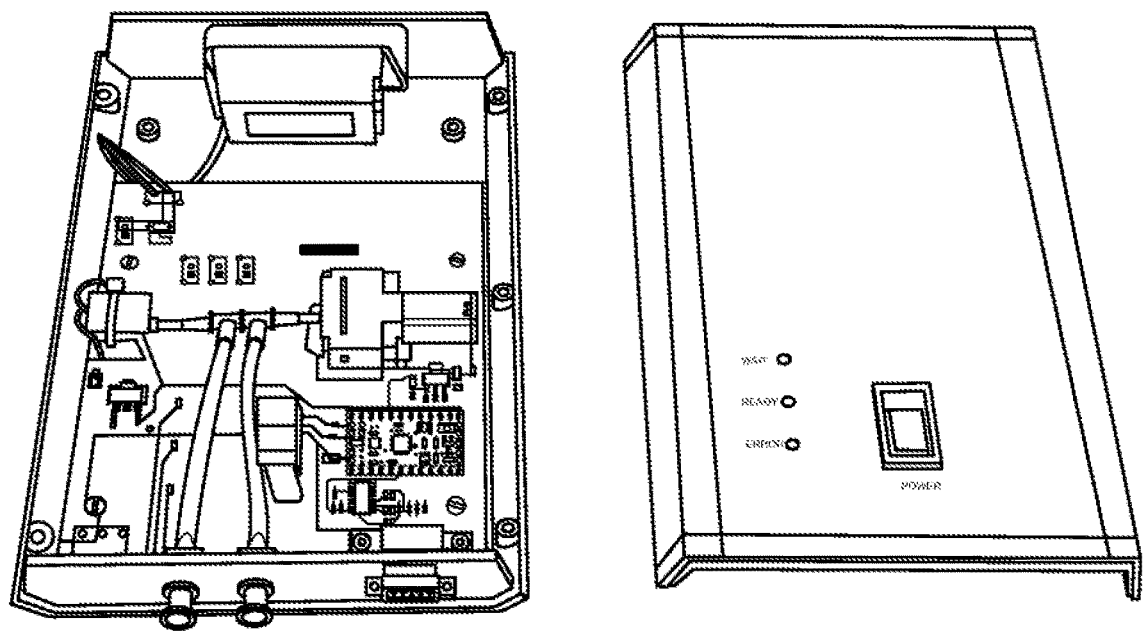
FIGS. 17A and 17B are front and top rear photographs, respectively, of the exemplary circuit board of FIG. 16 provided with an enclosure, forming an exemplary system according to an exemplary embodiment of the present disclosure.
Figure 17B:
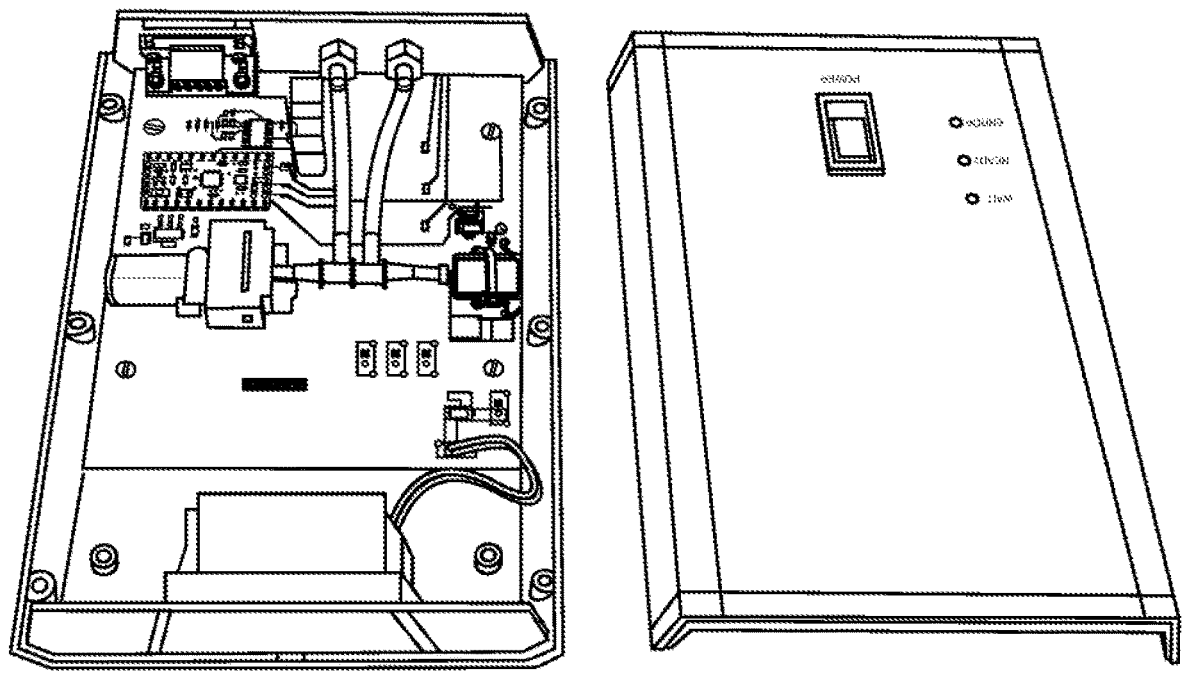

In additional exemplary embodiments of the present disclosure, another exemplary circuit board can be provided for the use with the exemplary system according to the present disclosure. For example, as shown in FIG. 16, such exemplary circuit board can be laid out for a top mounted power switch and LED indicators, and can be placed in a SERPAC enclosure, as shown in FIGS. 17A and 17B (providing top front and top rear views thereof). Holes can be machined to provide access to the internal works. Nomenclature can be silkscreened onto the enclosure. A 9V battery compartment on the rear of the exemplary enclosure provides for battery replacement without disassembly.

Figure 18:
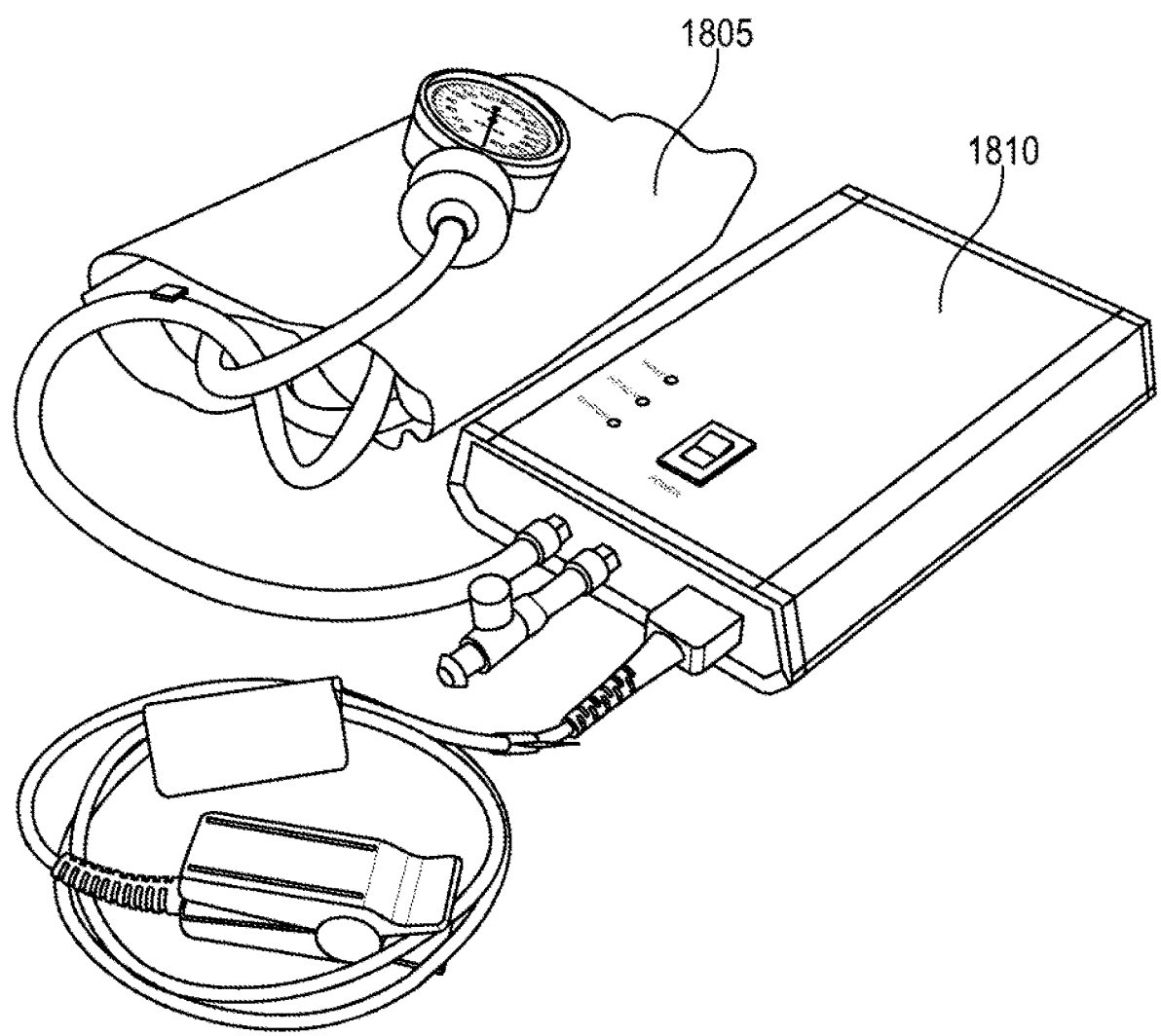
FIG. 18 is a photograph of an assembly of a blood pressure cuff that can be used with the exemplary system shown in FIGS. 16, 17A and 17B according to an exemplary embodiment of the present disclosure.

Thus, according to such exemplary embodiment of the present disclosure, as illustrated in FIG. 18, a standard blood pressure cuff 1805 can be used with the exemplary system 1810 shown in FIGS. 16, 17A and 17B. For example, the pump bulb can be removed, and the release valve and cuff can be attached using Luer connectors. The pressure gauge can be attached to the cuff. The finger sensor can be replaced by a Nelcor compatible $SpO_2$ adult finger unit and attached to the PST via, for example, a standard 9 pin serial port connector or using other known connectors.

Figure 19:
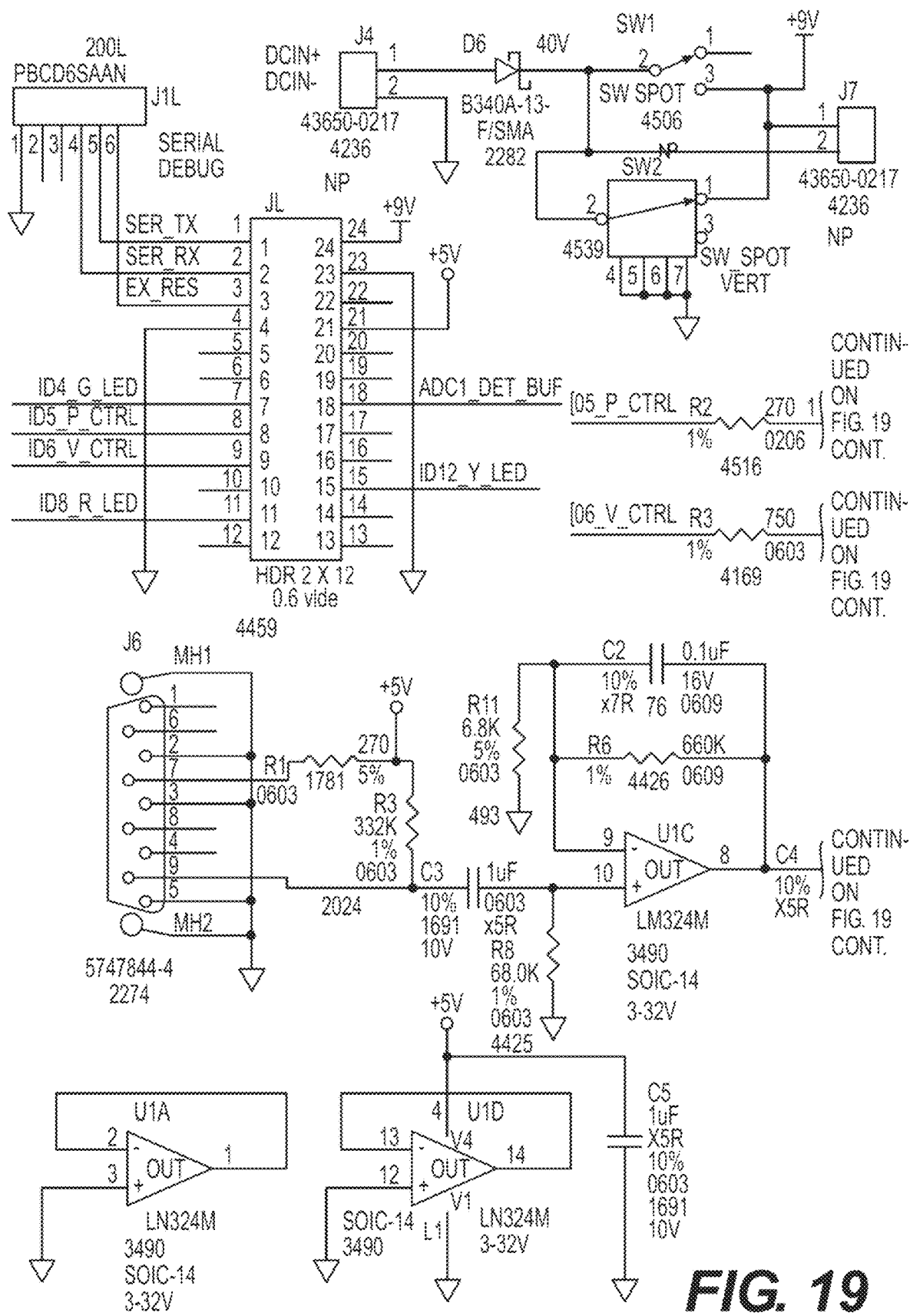
FIG. 19 is an exemplary schematic diagram of the exemplary circuit board illustrated in FIG. 16 according to an exemplary embodiment of the present disclosure.
Figure 19:
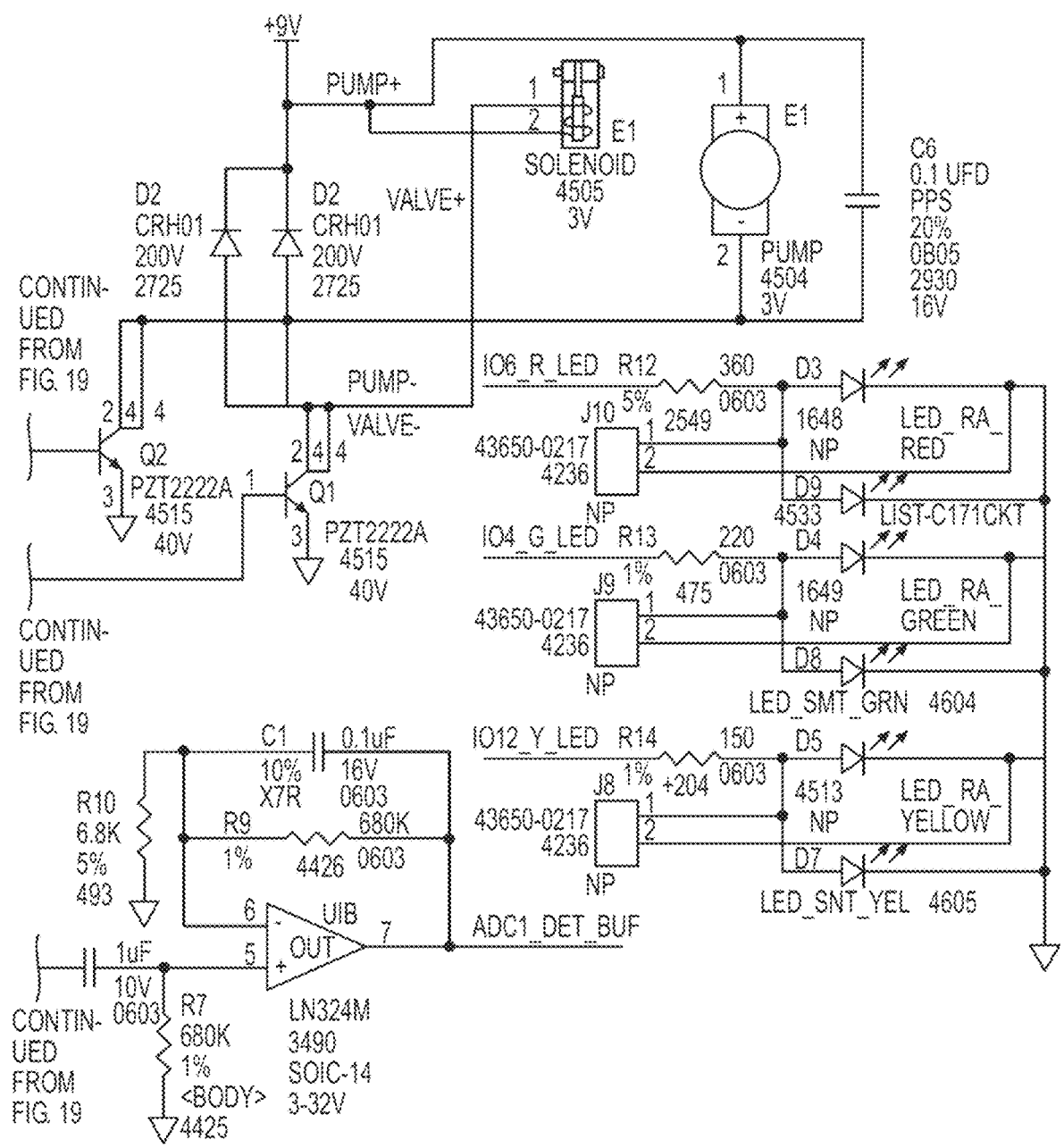
Figure 20B:
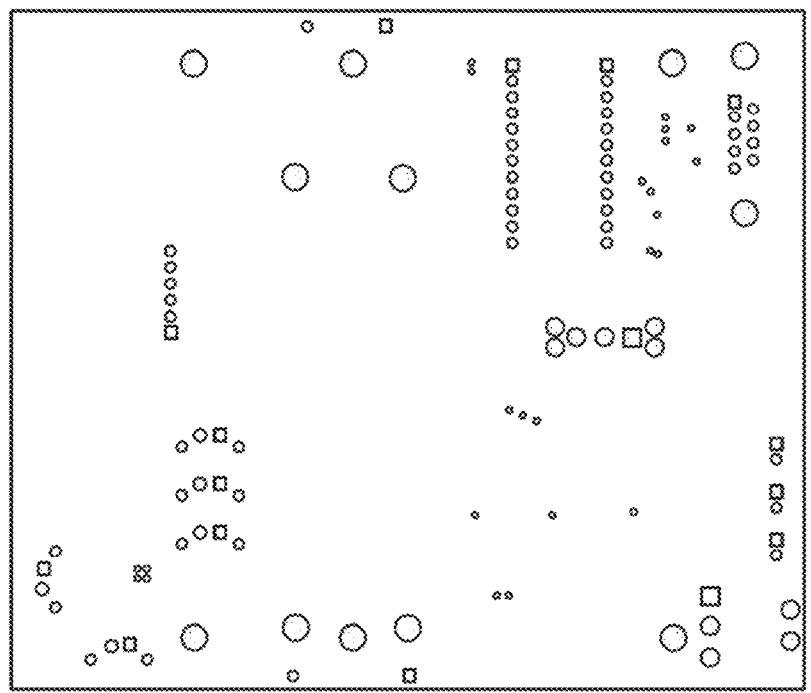
FIGS. 20A-20H are schematic diagrams of various view of sections of the layout of the exemplary printed circuit board of FIG. 16.
Figure 20A:
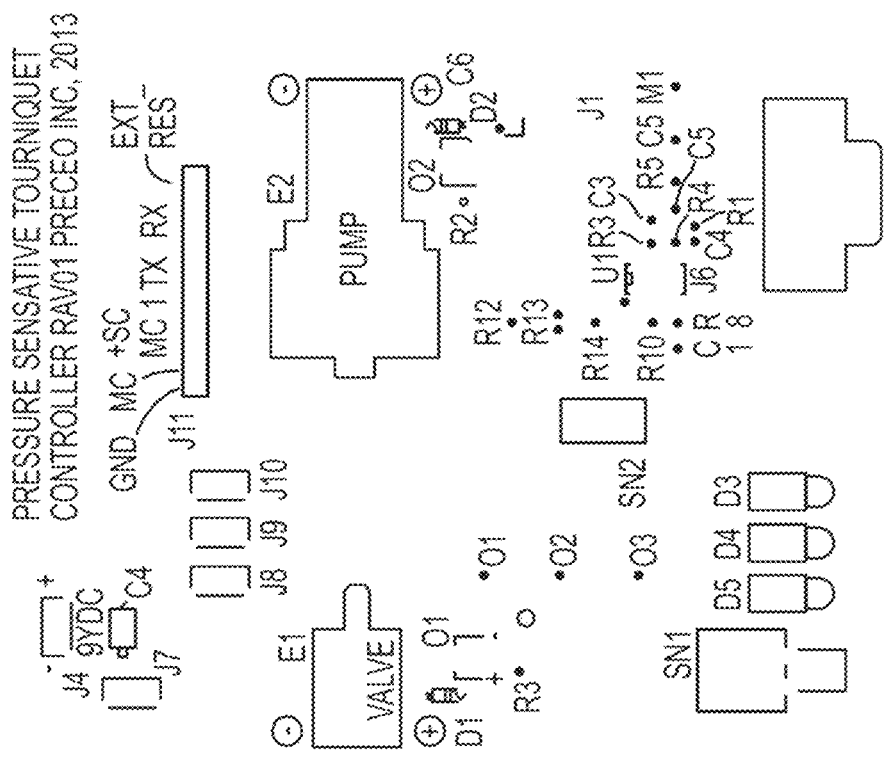
Figure 20D:
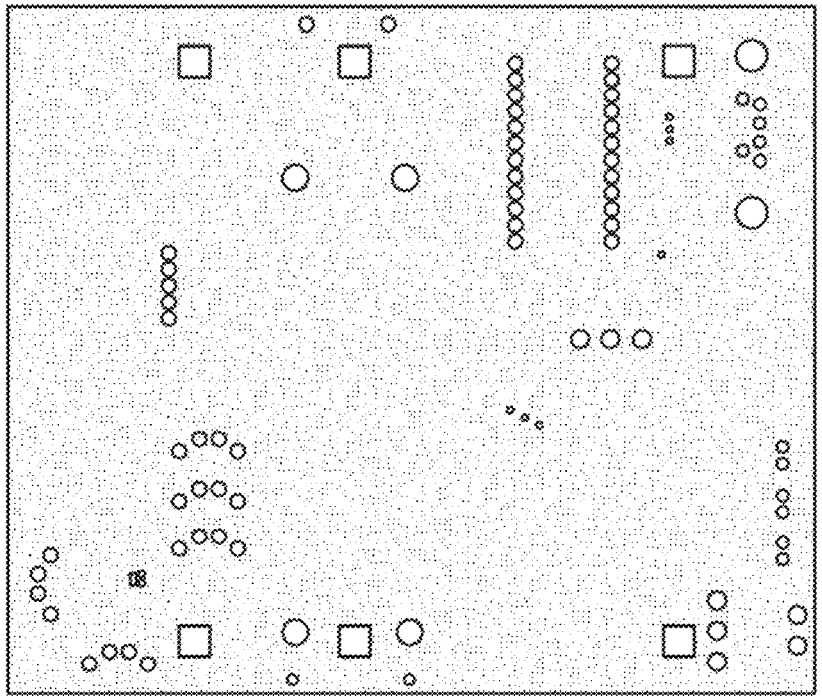
Figure 20C:
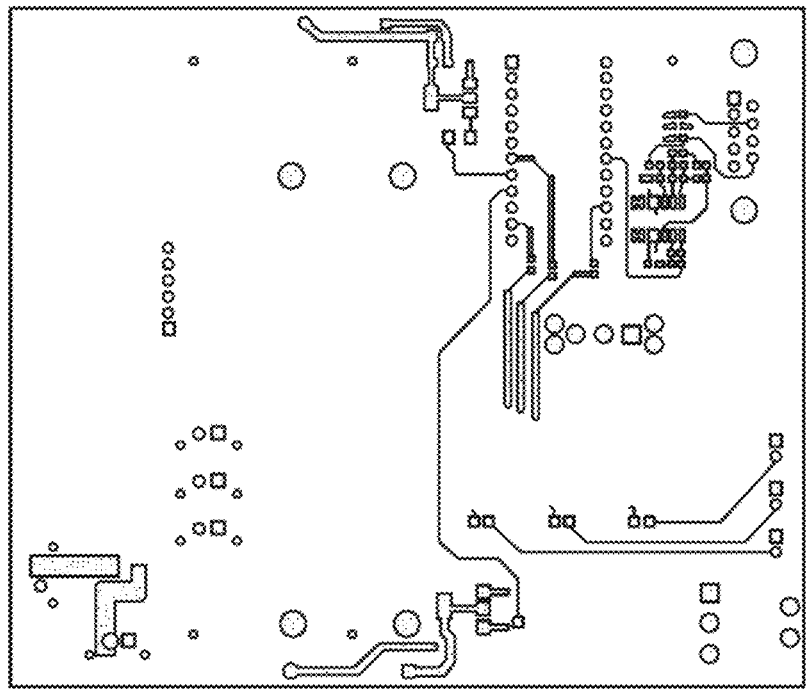
Figure 20F:
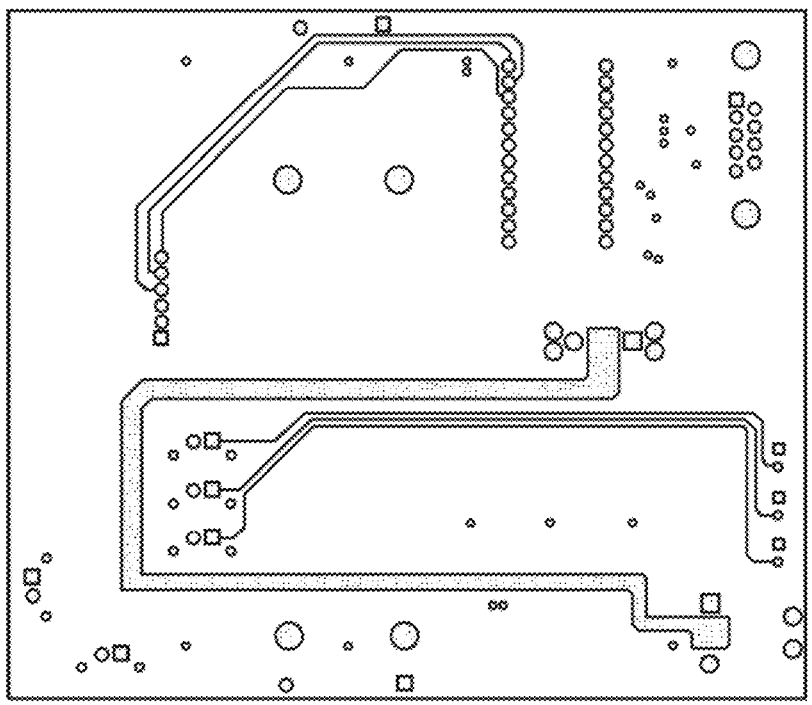
Figure 20E:
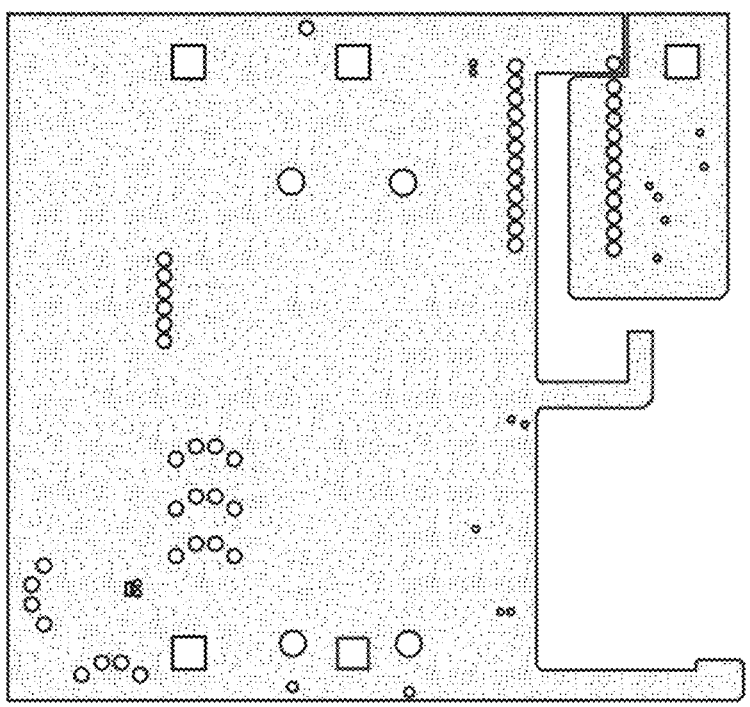
Figure 20H:
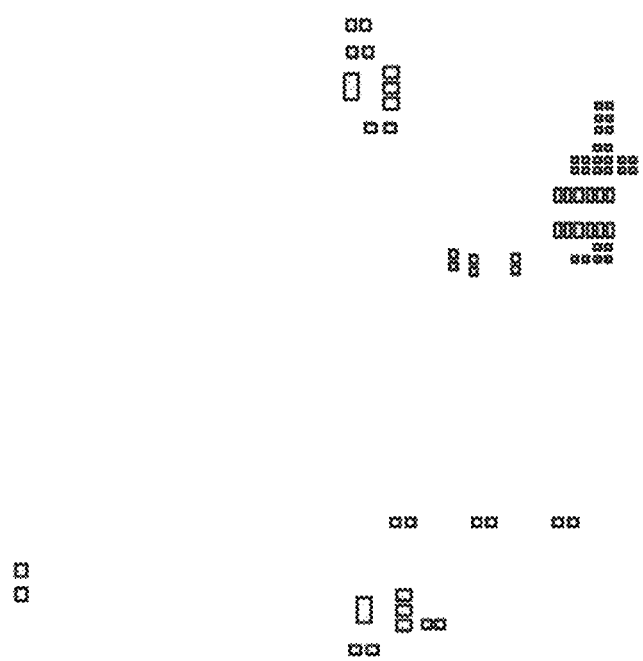
Figure 20G:
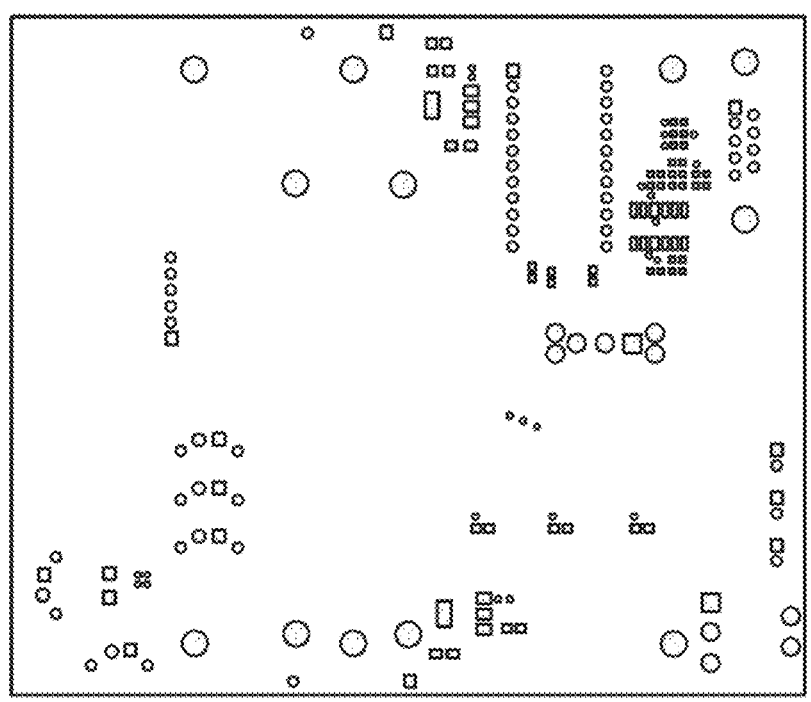

FIG. 19 shows an exemplary schematic diagram of the exemplary circuit board illustrated in FIG. 16, and FIGS. 20A-20H shows various view of sections of the layout of the exemplary printed circuit.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entirety.

[1] Steinke J M. Role of Light Scattering in Whole Blood Oximetry. *IEEE Transactions on Biomedical Engineering.* 1986; 33:294-301.

[2] Solid Angle—from Wolfram Math World. http://mathworld.wolfram.com/SolidAngle.html. Accessed Mar. 3, 2013.

[3] 4 mm Red/Orange/Green LEDs with Holders, RadioShack. http://www.radioshack.com/product/index.jsp?productId=2062568, http://www.radioshack.com/product/index.jsp?productId=2062570, and http://www.radioshack.com/product/index.jsp?productId=2062569. Accessed May 18, 2013.

[4] Bhandari N. A Simple Relationship between the Transistor Parameters hFE and hfe. *Proceedings of the IEEE.* 1967; 55:1099.

[5] NPN Transistor. http://i.stack.imgur.com/m9rv6.png. Accessed Feb. 24, 2013.

[6] Anderson A E. Transistors in Switching Circuits. *Proceedings of the IRE.* 1952; 40:1541-1558.

[7] KSV05A Solenoid Valve Data Sheet. http://www.koge.com/UploadFile/pdf/2011325142159-KSV05A.pdf. Accessed Feb. 24, 2013.

[8] KPM14A Air Pump Data Sheet. http://www.koge.com/UploadFile/pdf/2011324115349-KPM14A.pdf. Accessed Feb. 24, 2013.

[9] Serway R A and Jewett J W. Physics for Scientists and Engineers with Modern Physics. 7$^{th}$ ed. Thomson Learning. Belmont, 2008, pp 869.

[10] Serway R A and Jewett J W. Physics for Scientists and Engineers with Modern Physics. 7$^{th}$ ed. Thomson Learning. Belmont, 2008, pp 850.

[11] Serway R A and Jewett J W. Physics for Scientists and Engineers with Modern Physics. 7$^{th}$ ed. Thomson Learning. Belmont, 2008, pp 849.

[12] Magnetic Field Surrounding Solenoid. http://www.rf-cafe.com/references/electrical/Electricians%20Mate%203%20-%20Navy%20Training%20Courses%20%20NAVPERS%2010548/images/magnetic-field-surrounding-solenoid.jpg. Accessed Feb. 24, 2013.

[13] Pilliner G W. Protection and Safety. Part 6: Electromagnetic Problems. *Electronic Systems News.* 1988; 1988: 19-20.

[14] Tuskey G A, Yuan F, Katz D F. *Transport Phenomena in Biological Systems.* 2$^{nd}$ ed. Pearson Education. Upper Saddle River, 2009, pp 63.

[15] Tuskey G A, Yuan F, Katz D F. *Transport Phenomena in Biological Systems.* 2$^{nd}$ ed. Pearson Education. Upper Saddle River, 2009, pp 93.

[16] Holubkov R, Karas R H, Pepine C J, Rickens C R, Reichek N, Rogers W J, Sharaf B L, Sopko G, Merz C N, Kelsey S F, McGorray S P, and Reis S E. Large Brachial Artery Diameter is Associated with Angiographic Coronary Artery Disease in Women. *Am Heart J.* 2002; 143: 802-807.

[17] Spivack D E, Kelly P, Gaughan J P, and van Bemmelen P S. Mapping of Superficial Extremity Veins: Normal Diameters and Trends in a Vascular Patient-Population. *Ultrasound Med Biol.* 2012; 38:190-194.

[18] Tuskey G A, Yuan F, Katz D F. *Transport Phenomena in Biological Systems.* 2$^{nd}$ ed. Pearson Education. Upper Saddle River, 2009, pp 109.

[19] Ku D N. Blood Flow in Arteries. *Annual Review of Fluid Mechanics.* 1997; 29:399-434.

[20] Ethier C R and Simmons C A. Introductory Biomechanics: From Cells to Organisms. 1$^{st}$ ed. Cambridge University Press. Cambridge, 2007. pp 190.

[21] Weidinger F, Frick M, Alber H F, Ulmar H, Chwarzacher S P, and Pachinger O. Association of Wall Thickness of the Brachial Measured with High-Resolution Ultrasound with Risk Factors and Coronary Artery Disease. *Am J Cardiol.* 2002; 89:1025-1029.

[22] Jaberi A, Muradali D, Marticorena R M, Dacouris N, Boutin A, Mulligan A M, Ballyk P D, Prabhudesai V, Campbell V M, and Donnelly S M. Arteriovenous Fistulas for Hemodialysis: Application of High-Frequency US to Assess Vein Wall Morphology for Cannulation Readiness. *Radiology.* 2011; 261:616-624.

[23] Tracy R E and Eigenbrodt M L. Coronary Artery Circumferential Stress: Departure from Laplace Expectations with Aging. *Scientific World Journal.* 2009; 9:946-960.

[24] Arduino Mini. http://arduino.cc/en/uploads/Main/Mini05_front.jpg. Accessed May 18, 2013.

[25] Arduino Mini and NG Breadboard. http://arduino.cc/en/uploads/Guide/ArduinoMiniAndNGBreadboardPhoto.jpg. Accessed May 18, 2013.

What is claimed is:

1. An apparatus, comprising:
a cuff arrangement configured to apply a pressure around a limb of a patient;
a pump arrangement configured to control the pressure applied by the cuff arrangement;
a pulse detector arrangement; and
a computer hardware arrangement configured control the pump arrangement based on at least one of information or at least one signal provided from the pulse detector arrangement,
wherein the computer hardware arrangement controls the pump arrangement to (i) increase a pressure to reach a first pressure level corresponding to the pulse no longer being detected, (ii) decrease the pressure to reach a second pressure level corresponding to the pulse being again detected, (iii) stop decreasing the pressure once the pulse is again detected, and (iv) maintain the pressure to be substantially at the second pressure level to facilitate a venipuncture of at least one patient.

2. The apparatus of claim 1, wherein the pump arrangement includes at least one air pump and at least one solenoid valve.

3. The apparatus of claim 2, wherein the at least one solenoid valve is a normally open solenoid valve.

4. The apparatus of claim 1, wherein the pulse detector arrangement includes at least one pulse sensor.

5. The apparatus of claim 4, wherein the at least one pulse sensor includes at least one of (i) at least one infrared emitter and at least one infrared detector, or (ii) at least one auscultatory arrangement.

6. The apparatus of claim 1, further comprising at least one feedback arrangement configured to provide feedback from the apparatus.

7. The apparatus of claim 6, wherein the at least one feedback arrangement includes a light-emitting diode arrangement.

8. The apparatus of claim 6, wherein the feedback includes information regarding at least on of an error with the apparatus or that the apparatus is currently being operated.

9. The apparatus of claim 1, wherein the cuff arrangement includes an inflatable cuff.

10. The apparatus of claim 1, wherein the first pressure level corresponds to an arterial systolic pressure of the at least one patient.

11. The apparatus of claim 10, wherein the second pressure level corresponds to a pressure that is less than the arterial systolic pressure of the at least one patient and greater than an arterial diastolic pressure of the at least one patient.

12. The apparatus of claim 1, wherein the computer hardware arrangement is a microcontroller.

13. A non-transitory computer-accessible medium having stored thereon computer-executable instructions for facilitating a venipuncture of at least one patient, wherein, when a computer hardware arrangement executes the instructions, the instructions allow the computer hardware arrangement to perform procedures comprising:
receiving information related to a detection of a pulse of the at least one patient detected by a pulse detector;
increasing a pressure applied externally to the at least one patient using the computer hardware arrangement by controlling a pump arrangement to reach a first pressure level corresponding to the pulse no longer being detected by the pulse detector;
decreasing the pressure provided by the computer hardware arrangement by controlling the pump arrangement to reach a second pressure level corresponding to the pulse being again detected by the pulse detector;
stopping the decrease of the pressure one the pulse is again detected by the pulse detector; and maintaining the pressure to be substantially at the second pressure level to facilitate a venipuncture of the at least one patient.

14. The computer-accessible medium of claim 13, wherein the first pressure level corresponds to an arterial systolic pressure of the at least one patient.

15. The computer-accessible medium of claim 14, wherein the second pressure level corresponds to a pressure that is less than the arterial systolic pressure of the at least one patient and greater than an arterial diastolic pressure of the at least one patient.

16. The computer-accessible medium of claim 13, wherein the computer hardware arrangement is further configured to generate additional information using the pulse detector.

17. The computer-accessible medium of claim 13, wherein the pump arrangement includes at least one air pump and at least one solenoid valve.

18. A method for facilitating a venipuncture of at least one patient, comprising:

receiving information related to a detection of a pulse of the at least one patient;

increasing a pressure applied externally to the at least one patient using a computer hardware arrangement to reach a first pressure level corresponding to the pulse no longer being detected;

decreasing the pressure provided by the computer hardware arrangement to reach a second pressure level corresponding to the pulse being again detected;

stopping the decrease of the pressure once the pulse is again detected; and using the computer hardware arrangement, maintaining the pressure to be at the second pressure level to facilitate a venipuncture of the at least one patient.

19. The method of claim 18, wherein the first pressure level corresponds to an arterial systolic pressure of the at least one patient, and wherein the second pressure level corresponds to a pressure that is less than the arterial systolic pressure of the at least one patient and greater than an arterial diastolic pressure of the at least one patient.

* * * * *